US009060842B2

(12) United States Patent
Karp et al.

(10) Patent No.: US 9,060,842 B2
(45) Date of Patent: Jun. 23, 2015

(54) ADHESIVE ARTICLES

(75) Inventors: Jeffrey Karp, Brookline, MA (US); Mahdavi Alborz, Markham (CA); Lino Ferreira, Coimbra (PT); David Carter, Concord, MA (US); Andreas Zumbuehl, Nyon (CH); Jeffrey Borenstein, Newton, MA (US); Edwin Chan, Montgomery Village, MD (US); Christopher Bettinger, Pittsburgh, PA (US); Robert Langer, Newton, MA (US)

(73) Assignees: Massachusettes Institute of Technology, Cambridge, MA (US); The Charles Stark Draper Laboratory, Inc., Cambridge, MA (US)

( * ) Notice: Subject to any disclaimer, the term of this patent is extended or adjusted under 35 U.S.C. 154(b) by 640 days.

(21) Appl. No.: 12/743,817

(22) PCT Filed: Nov. 19, 2008

(86) PCT No.: PCT/US2008/083980
§ 371 (c)(1),
(2), (4) Date: Oct. 15, 2010

(87) PCT Pub. No.: WO2009/067482
PCT Pub. Date: May 28, 2009

(65) Prior Publication Data
US 2011/0021965 A1    Jan. 27, 2011

Related U.S. Application Data

(60) Provisional application No. 60/989,101, filed on Nov. 19, 2007.

(51) Int. Cl.
*A61L 15/58* (2006.01)
*B29C 65/52* (2006.01)
(Continued)

(52) U.S. Cl.
CPC .............. *A61F 2/0077* (2013.01); *B29C 65/52* (2013.01); *B29C 66/1122* (2013.01); *B31B 19/90* (2013.01);
(Continued)

(58) Field of Classification Search
CPC ..................................................... A61L 15/58
USPC ........... 442/59, 149, 151, 150, 181, 295, 299, 442/FOR. 100, FOR. 101, FOR. 121, 442/FOR. 136, FOR. 137; 602/54, 42, 41, 602/55; 428/32.6, 32.77, 32.78, 32.79, 428/40.1, 41.9, 64.1, 64.2, 64.4, 65.2, 98, 428/212–214; 156/1, 60, 290, 291, 325, 66; 606/213–214; 424/443–449
See application file for complete search history.

(56) References Cited

U.S. PATENT DOCUMENTS 4,057,535 A * 11/1977 Lipatova et al. ................. 528/68
5,011,494 A     4/1991  vonRecum
(Continued)

FOREIGN PATENT DOCUMENTS

EP          0259536          3/1988

*Primary Examiner* — Alireza Nia
*Assistant Examiner* — Tarla Patel
(74) *Attorney, Agent, or Firm* — Pabst Patent Group LLP

(57) ABSTRACT

An adhesive article includes a biocompatible and at least partially biodegradable substrate having a surface; and a plurality of protrusions extending from the surface. The protrusions include a biocompatible and at least partially biodegradable material, and have an average height of less than approximately 1,000 micrometers.

14 Claims, 12 Drawing Sheets

(51) Int. Cl.
*A61F 2/00* (2006.01)
*A61L 15/42* (2006.01)
*A61L 15/64* (2006.01)
*A61L 31/00* (2006.01)
*A61L 31/14* (2006.01)
*B29C 65/00* (2006.01)
*B31B 19/90* (2006.01)
*C04B 37/00* (2006.01)
*B29C 65/18* (2006.01)
*A61F 2/30* (2006.01)
*A61F 13/00* (2006.01)
*A61K 9/00* (2006.01)

(52) U.S. Cl.
CPC ............... *C04B 37/005* (2013.01); *B29C 65/18* (2013.01); *A61F 2002/30448* (2013.01); *A61F 2013/00774* (2013.01); *A61F 2220/005* (2013.01); *A61K 9/0019* (2013.01); *A61L 15/42* (2013.01); *A61L 15/58* (2013.01); *A61L 15/64* (2013.01); *A61L 31/005* (2013.01); *A61L 31/14* (2013.01); *A61L 31/148* (2013.01); *A61F 2220/0016* (2013.01)

(56) References Cited

U.S. PATENT DOCUMENTS

| | | | |
|---|---|---|---|
| 5,348,788 | A | 9/1994 | White |
| 6,720,469 | B1 | 4/2004 | Curtis |
| 6,759,110 | B1 * | 7/2004 | Fleming et al. ............... 428/41.8 |
| 6,872,439 | B2 * | 3/2005 | Fearing et al. .................. 428/99 |
| 7,217,294 | B2 * | 5/2007 | Kusanagi et al. ........... 623/18.11 |
| 7,396,976 | B2 * | 7/2008 | Hurwitz et al. ............. 602/58 |
| 2003/0178124 | A1 * | 9/2003 | Mikami et al. .................. 156/87 |
| 2003/0221778 | A1 * | 12/2003 | Musch et al. ................ 156/325 |
| 2004/0048024 | A1 * | 3/2004 | Fleming et al. .............. 428/40.1 |
| 2004/0213941 | A1 * | 10/2004 | Whitehouse ................ 428/40.1 |
| 2005/0203637 | A1 | 9/2005 | Edman |
| 2005/0227031 | A1 * | 10/2005 | Yang et al. ................... 428/40.1 |
| 2006/0204738 | A1 | 9/2006 | Dubrow |
| 2007/0123973 | A1 * | 5/2007 | Roth et al. ................... 623/1.15 |
| 2007/0161109 | A1 | 7/2007 | Archibald |
| 2008/0280085 | A1 * | 11/2008 | Livne .......................... 428/40.1 |
| 2009/0130372 | A1 * | 5/2009 | Fukui et al. ..................... 428/92 |
| 2012/0052234 | A1 | 3/2012 | Natarajan et al. |

* cited by examiner

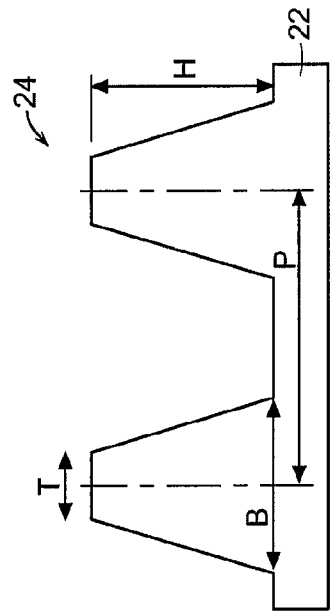
FIG. 1
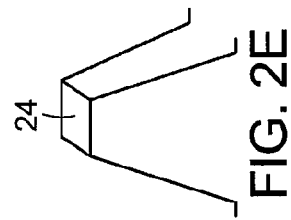
FIG. 2A
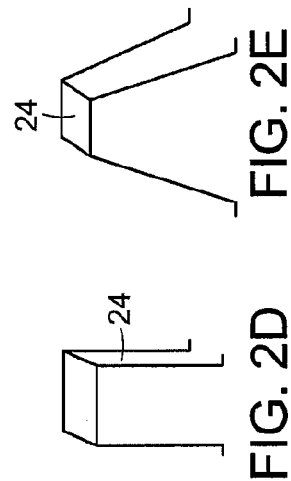
FIG. 2B
FIG. 2C
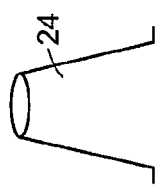
FIG. 2D
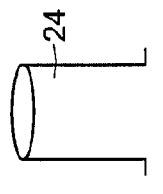
FIG. 2E
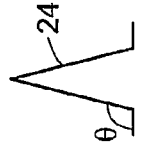
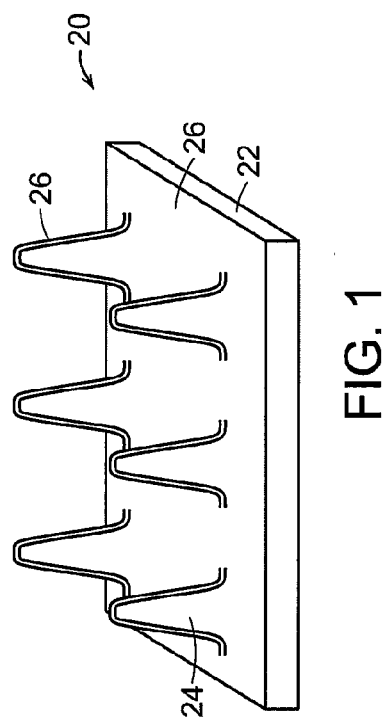
FIG. 3

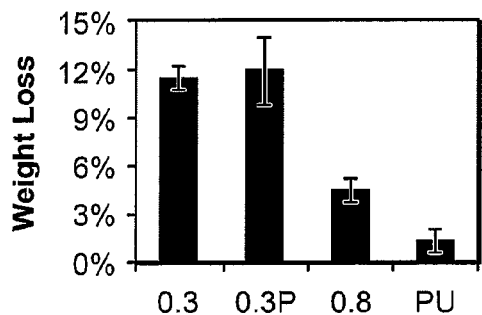
FIG. 11A
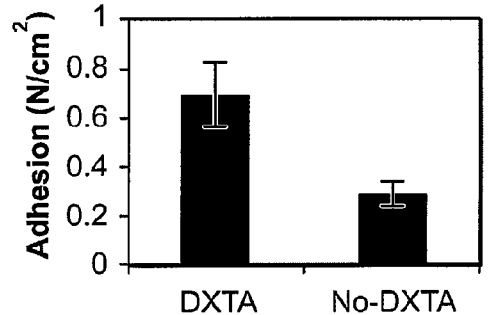
FIG. 11B
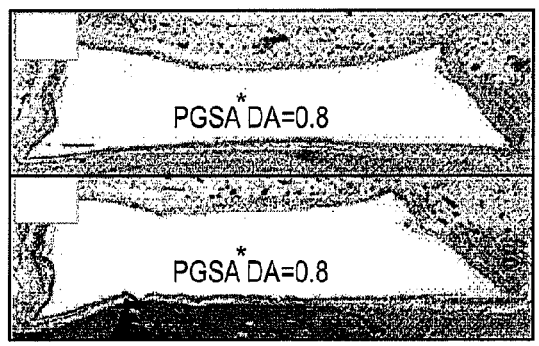
FIG. 11C
FIG. 11D
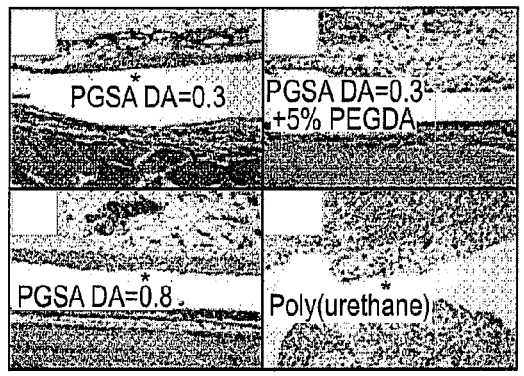
FIG. 11E  FIG. 11F
FIG. 11G  FIG. 11H

ADHESIVE ARTICLES

CROSS-REFERENCE TO RELATED APPLICATION

This application is a national filing under 35 U.S.C. 371 of International Application No. PCT/US2008/083980 (PCT Publication No. WO 2009/067482), filed Nov. 19, 2008, which claims priority to U.S. Provisional Patent Application 60/989,101, filed on Nov. 19, 2007, and entitled "Microstructured Adhesive Articles", hereby incorporated by reference.

GOVERNMENT SUPPORT

The United States Government has provided grant support utilized in the development of one or more of the present inventions. In particular, National Institute of Health (NIH) contract number DE 013023, National Science Foundation (NSF) contract number NIRT 0609182, and the MRSEC Program of the National Science Foundation under award number DMR 02-1328 have supported development of one or more of the inventions of the present application. The United States Government may have certain rights in these inventions.

TECHNICAL FIELD

The invention relates to adhesive articles.

BACKGROUND

Tissue adhesives have a variety of medical applications, such as wound healing sealants, adhesion barriers, and drug delivery patches. Some tissue adhesives, such as those based on cyanoacrylates, fibrin, collagen and other formulations including proteins or polyurethane pre-polymers, can have limited applications due to problems associated with histotoxicity, cytotoxicity, carcinogenicity, and risk of embolization or intravascular coagulation. Additionally, the mechanical properties of certain adhesives do not match the underlying tissue, which can limit their long-term effectiveness.

SUMMARY

The invention relates to adhesive articles.

In one aspect, the invention features adhesive articles that are tough, biocompatible, biodegradable, flexible, elastic and able to form strong bonds to surfaces (e.g., tissue), even in a moist or wet environment.

In another aspect, the invention features adhesive articles having modified morphology and/or chemistry (e.g., surface morphology and/or chemistry) that mimic the nanoscale topography of gecko feet that allows the gecko to attach to surfaces (e.g., vertical surfaces). For example, morphologically, the adhesive articles include protrusions that mimic setae (or fibrils) and spatulae (or terminal projections) found on the footpads of geckos. The arrangement and dimensional parameters (e.g., tip width to pitch ratio, or tip width to base width ratio) of the protrusions can be controlled and optimized to enhance adhesion. Chemically, in some embodiments, the adhesive articles include a thin, tissue reactive, biocompatible surface coating. As described below, coating the adhesive articles with, for example, a thin layer of oxidized dextran can significantly increased the interfacial adhesion strength on porcine intestine tissue in vitro and in the rat abdominal subfascial in vivo environment.

In another aspect, the invention features an adhesive article including a biocompatible and at least partially biodegradable substrate having a surface; and a plurality of protrusions extending from the surface. The protrusions include a biocompatible and biodegradable material, and have an average height of less than approximately 1,000 micrometers.

In another aspect, the invention features an adhesive article including a substrate having a surface; and a plurality of protrusions extending from the surface. The protrusions include a material that is suitable for short-term (e.g., less than approximately 3 weeks, less than approximately 2 weeks, less than approximately 1 week) application inside or outside a body, and have an average height of less than approximately 1,000 micrometers.

In another aspect, the invention features an adhesive article including an at least partially biodegradable substrate having a surface; and a plurality of protrusions extending from the surface. The article is capable of exerting minimal chronic inflammation when the article is implanted in vivo. In some embodiments, the protrusions have an average height of less than approximately 1,000 micrometers.

In another aspect, the invention features an adhesive article including an at least partially biodegradable substrate having a surface; and a plurality of protrusions extending from the surface. The article includes portions (such as the substrate and/or the protrusions) having different degradation properties (such as degradation rates). In some embodiments, the protrusions have an average height of less than approximately 1,000 micrometers.

In another aspect, the invention features an adhesive article including a substrate having a surface; and a plurality of protrusions extending from the surface. The article includes a composition that allows the article to be tolerated by the body when the article is applied inside or outside the body. In some embodiments, the protrusions have an average height of less than approximately 1,000 micrometers.

In another aspect, the invention features an adhesive article including a biocompatible and at least partially biodegradable substrate having a surface; protrusions extending from the surface, the protrusions including a biocompatible and at least partially biodegradable material, and having an average height of less than approximately 1,000 micrometers.

In another aspect, the invention features a method including contacting an adhesive article to biological tissue, the adhesive article including a biocompatible and at least partially biodegradable substrate having a surface; and protrusions extending from the surface, the protrusions having a biocompatible and at least partially biodegradable material, and having an average height of less than approximately 1,000 micrometers.

In another aspect, the invention features an adhesive article including a substrate having a surface; protrusions extending from the surface, the protrusions having an average height of less than approximately 1,000 micrometers; and a material on the substrate and/or the protrusions, the material capable of covalently bonding to a site to which the adhesive article is applied.

In another aspect, the invention features a method including contacting an adhesive article to biological tissue, the adhesive article including a substrate having a surface; and protrusions extending from the surface, the protrusions having an average height of less than approximately 1,000 micrometers; and piercing the tissue with the protrusions.

Embodiments of the aspects of the invention may include one or more of the following features. The adhesive article further includes a surface modification that enhances bonding of said surface to biological tissue. The surface modification is capable of forming a chemical bond with the biological tissue. The chemical bond is a covalent bond. The covalent bond includes a reaction including an amine group and/or a hydroxyl group. The surface modification includes dextran or modified dextran. The surface modification includes a functionality capable of covalently bonding to the biological tissue, the functionality being selected from the group consisting of a carbonyl, an aldehyde, an acrylate, a cyanoacrylate, an epoxy, N-hydroxysuccinimide, and an oxirane.

The substrate and/or the protrusions can include a material selected from the group consisting of poly(glycerol sebacate) (PGS), poly(glycerol sebacate acrylate) (PGSA), poly(lactic-co-glycolic acid) (PLGA), polycaprolactone (PCL), polyglycolide (PGA), polylactic acid (PLA), and/or poly-3-hydroxybutyrate (PHB), polyurethane, parylene-C, keratin, carbon nanotubes, poly(anhydride), and chitosan.

The protrusions can have an average height of from approximately 0.2 μm to approximately 10 μm. For example, the average height can be greater than or equal to approximately 0.05 μm, approximately 1 μm, approximately 2 μm, approximately 3 μm, approximately 4 μm, approximately 5 μm, approximately 6 μm, approximately 7 μm, approximately 8 μm, or approximately 9 μm; and/or less than or equal to approximately 10 μm, approximately 9 μm, approximately 8 μm, approximately 7 μm, approximately 6 μm, approximately 5 μm, approximately 4 μm, approximately 3 μm, approximately 2 μm, or approximately 1 μm.

The protrusions can have an average tip width of from approximately 0.05 μm to approximately 10 μm. For example, the average tip width can be greater than or equal to approximately 0.05 μm, approximately 1 μm, approximately 2 μm, approximately 3 μm, approximately 4 μm, approximately 5 μm, approximately 6 μm, approximately 7 μm, approximately 8 μm, or approximately 9 μm; and/or less than or equal to approximately 10 μm, approximately 9 μm, approximately 8 μm, approximately 7 μm, approximately 6 μm, approximately 5 μm, approximately 4 μm, approximately 3 μm, approximately 2 μm, or approximately 1 μm.

The protrusions can have an average base width of from approximately 0.05 μm to approximately 10 μm. For example, the average base width can be greater than or equal to approximately 0.05 μm, approximately 1 μm, approximately 2 μm, approximately 3 μm, approximately 4 μm, approximately 5 μm, approximately 6 μm, approximately 7 μm, approximately 8 μm, or approximately 9 μm; and/or less than or equal to approximately 10 μm, approximately 9 μm, approximately 8 μm, approximately 7 μm, approximately 6 μm, approximately 5 μm, approximately 4 μm, approximately 3 μm, approximately 2 μm, or approximately 1 μm.

The protrusions can have an average center-to-center pitch of from approximately 0.2 μm to approximately 500 μm. For example, the average center-to-center pitch can be greater than or equal to approximately 0.2 μm, approximately 25 μm, approximately 50 μm, approximately 100 μm, approximately 150 μm, approximately 200 μm, approximately 250 μm, approximately 300 μm, approximately 350 μm, approximately 400 μm, or approximately 450 μm; and/or less than or equal to approximately 500 μm, approximately 450 μm, approximately 400 μm, approximately 350 μm, approximately 300 μm, approximately 250 μm, approximately 200 μm, approximately 150 μm, approximately 100 μm, approximately 50 μm, or approximately 25 μm.

The protrusions can have an average height to base width ratio of from approximately 0.1:1 to approximately 500:1. For example, the average height to base width ratio can be greater than or equal to approximately 0.1:1, approximately 25:1, approximately 50:1, approximately 100:1, approximately 150:1, approximately 200:1, approximately 250:1, approximately 300:1, approximately 350:1, or approximately 450:1; and/or less than or equal to approximately 500:1, approximately 450:1, approximately 400:1, approximately 350:1, approximately 300:1, approximately 250:1, approximately 200:1, approximately 150:1, approximately 100:1, approximately 50:1, or approximately 25:1.

The protrusions can have average base width to tip width ratio of from approximately 1000:1 to approximately 0.1:1. For example, the average base width to tip width ratio can be greater than or equal to approximately 0.1:1, approximately 25:1, approximately 50:1, approximately 100:1, approximately 150:1, approximately 200:1, approximately 250:1, approximately 300:1, approximately 350:1, approximately 450:1, approximately 500:1, approximately 550:1, approximately 600:1, approximately 650:1, approximately 700:1, approximately 750:1, approximately 800:1, approximately 850:1, approximately 900:1, approximately 950:1, and/or less than or equal to approximately 1000:1, approximately 950:1, approximately 900:1, approximately 850:1, approximately 800:1, approximately 750:1, approximately 700:1, approximately 650:1, approximately 600:1, approximately 550:1, approximately 500:1, approximately 450:1, approximately 400:1, approximately 350:1, approximately 300:1, approximately 250:1, approximately 200:1, approximately 150:1, approximately 100:1, approximately 50:1, or approximately 25:1.

At least a portion of the adhesive article can have an adhesive strength of greater than approximately 0.1 Newton per square centimeter of projected area when measured according to ASTM standard D4501.

At least a portion of the adhesive article can have a wet adhesive strength that is greater than or substantially equal to a dry adhesive strength.

The substrate and/or the protrusions can include a material that is not biodegradable. For example, the non-biodegradable material can be used to enhance one or more properties of the adhesive article, such as strength. The non-biodegradable material can be intimately mixed with one or more biodegradable materials. Alternatively or additionally, the adhesive article can include discrete portions (e.g., layers) of non-biodegradable material and biodegradable material. These intimate mixtures and/or discrete portions can make the substrate and/or the protrusions, independently.

The substrate and/or the protrusions can include a biomolecule or a pharmaceutical compound. The pharmaceutical compound can be selected from the group consisting of anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and pro- or anti-adhesion molecules, vasodilating agents, inhibitors of DNA, RNA or protein synthesis, anti-hypertensives, analgesics, anti-pyretics, steroidal and non-steroidal anti-inflammatory agents, pro- or anti-angiogenic factors, pro- or anti-secretory factors, anticoagulants and/or antithrombotic agents, local anesthetics, ophthalmics, prostaglandins, anti-depressants, anti-psychotic substances, anti-emetics, growth factors, proton pump inhibitors, hormones, vitamins, gene delivery systems, and imaging agents.

The adhesive article can have a maximum elongation greater than approximately 20%.

At least a portion of the adhesive article can have a porosity of greater than approximately 10%.

At least a portion of the adhesive article can have an average pore size in the range from approximately 10 nm to approximately 1 micrometer.

At least a portion of the adhesive article can include a plurality of cells. The cells can include one or more kerotinocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, stem cells, neurobalstoma, chondrocytes, skin cells and bone-forming cells.

The adhesive article can be in the form of a tape.

The substrate can include portions of different compositions. The portions can be discrete layers.

The substrate can include portions having different degradation rates. The portions can be discrete layers.

The protrusions can include portions of different compositions. The portions can be discrete layers.

The protrusions can include portions having different degradation rates. The portions can be discrete layers.

The adhesive article can further include a second set of protrusions extending from the protrusions.

The biological tissue can include one or more of an epithelium tissue, connective tissue, myocardium tissue, muscular tissue, organ tissue, damaged tissue, scar tissue, and nervous tissue.

The methods can further include chemically bonding at least a portion of the adhesive article to the biological tissue.

The methods can further include wrapping the adhesive article around biological tissue.

The protrusions can penetrate into the biological tissue.

In the methods, the adhesive article can connect at least two different biological tissues.

In the methods, the adhesive article can connect tissue and a device (e.g, a drug delivery device, an oral appliance, or a sensor).

Embodiments of aspects of the invention may include one or more of the following features or advantages.

The biocompatibility, biodegradation, adhesiveness, compliance and conformability to tissue surfaces properties of the adhesive articles can be controlled and tuned appropriately for a targeted application site (e.g., tissue). Each and every component of the adhesive articles can be designed and tailored for use with an intended application site. For example, the composition, chemical modification (e.g., degree of cross-linking density), and dimensional parameters (e.g., thickness) of the substrate, protrusions, and/or surface modification can be independently designed and tailored to an intended application.

In some embodiments, the wet adhesive strength of the adhesive articles (e.g., when contacting water and/or in contact with a wet surface (e.g., such as a biological tissue)) is greater than the dry adhesive strength of the articles (e.g., when not contacting water, and/or when in air, e.g., in contact with a dry surface, e.g., such as a silicon surface (e.g., glass, borosilicate, silicon nitride, etc.)).

Embodiments of the adhesive articles, can be used in a variety of medical applications, including, but not limited to, one or more of: wound closure or sealing, tissue affixation (e.g., in addition to or as a replacement for sutures and staples), bioactive agent delivery vehicles (e.g., delivery of antibiotics, drugs, etc), waterproof sealants for hollow organ anastomoses, mesh grafts to treat hernias, ulcers, burns, and haemostatic wound dressings, patches for diabetic ulcers, abdominal implant to prevent adhesions, biodegradable adhesive, in vivo and in vitro sensors, catheters, surgical glue, cardiac, bile-duct, intestinal stent, coatings for metals, microfabrication applications, long-term circulating particles for applications including targeted drug delivery, blood substitutes etc., injectable drug delivery system for mechanically taxing environments (e.g., within joints) where, for example, the material can be configured to release drugs in controlled manner without being compromised by a dynamic or static external environment, degradable O-rings, septa etc. The adhesive articles can adapt to, or recover from various mechanical deformations while remaining strongly attached to the underlying tissue.

Adhesion in a dry environment can be achieved without a chemical "glue".

The adhesive articles can have enhanced interface compliance and conformability to surfaces with a variety of roughness.

The adhesive articles can provide strong irreversible bonds to organic substrates, e.g., to avoid disruption by the movement of underlying or nearby tissues, such as for medical applications. In some embodiments, the articles can be bonded (e.g., covalently cross-linked or bonded) to wet tissue.

Other aspects, features and advantages will be apparent from the description of the embodiments thereof and from the claims.

DEFINITIONS

As used herein, the article "a" is used in its indefinite sense to mean "one or more" or "at least one." That is, reference to any element of the present teachings by the indefinite article "a" does not exclude the possibility that more than one of the element is present.

The term "amide" or "aminocarboxy" includes compounds or groups that contain a nitrogen atom that is bound to the carbon of a carbonyl or a thiocarbonyl group. The term includes "Alkylaminocarboxy" groups that include alkyl, alkenyl, or alkynyl groups bound to an amino group bound to a carboxy group. It includes arylaminocarboxy groups that include aryl or heteroaryl groups bound to an amino group which is bound to the carbon of a carbonyl or thiocarbonyl group. The terms "alkylaminocarboxy," "alkenylaminocarboxy," "alkynylaminocarboxy," and "arylaminocarboxy" include groups wherein alkyl, alkenyl, alkynyl and aryl groups, respectively, are bound to a nitrogen atom which is in turn bound to the carbon of a carbonyl group.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

As used herein, "biocompatible" refers to the ability of a structure or a material to perform its desired function with respect to a medical therapy, without eliciting any undesirable local or systemic effects in the recipient or beneficiary of that therapy, but generating the most appropriate beneficial cellular or tissue response in that specific situation, and optimizing the clinically relevant performance of that therapy. (See Williams, *Biomaterials* 29 (2008) 2941-2953). In some embodiments, "biocompatible" means not toxic to cells. In some embodiments, a substance is considered to be "biocompatible" if its addition to cells in vivo does not induce inflammation and/or other adverse effects in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

As used herein, the term "biodegradable" refers to substances that are degraded under physiological conditions. In some embodiments, a biodegradable substance is a substance that is broken down (e.g., when introduced into cells, in vivo) by the cellular machinery and/or by chemical processes (e.g., hydrolysis, enzyme mediated degradation, and/or oxidative mediated degradation) into components that can either be re-used and/or disposed of without significant toxic effect (e.g., on cells (e.g., fewer than about 20% of the cells are killed when the components are added to cells in vitro)). The components typically do not induce inflammation or other adverse effects in vivo. The components can be molecular species and/or fragments of the substance. In some embodiments, the chemical reactions relied upon to break down the biodegradable compounds are uncatalyzed. As examples, "biodegradable" polymers are polymers that degrade to other species (e.g., monomeric and/or oligomeric species) under physiological or endosomal or lysosomal conditions. The polymers and polymer biodegradation products can be biocompatible. Biodegradable polymers are not necessarily hydrolytically degradable and may require enzymatic action to fully degrade. Biodegradation mechanisms can include, for example, hydrolytic degradation, enzymatic degradation, and mechanisms in which the environment naturally introduces degradation factors, and/or where a catalyst is introduced to trigger degradation.

As used herein, the term "biological tissue" refers to a collection of similar cells combined to perform a specific function, and can include any extracellular matrix surrounding the cells.

The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, RNA, proteins, peptides, polysaccharides and any combinations of these components.

The term "carbonyl" or "carboxy" includes compounds and groups which contain a carbon connected with a double bond to an oxygen atom, and tautomeric forms thereof. Examples of groups that contain a carbonyl include aldehydes, ketones, carboxylic acids, amides, esters, anhydrides, etc. The term "carboxy group" or "carbonyl group" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl group. For example, the term includes groups such as, for example, aminocarbonyl groups, (wherein a nitrogen atom is bound to the carbon of the carbonyl group, e.g., an amide), aminocarbonyloxy groups, wherein an oxygen and a nitrogen atom are both bond to the carbon of the carbonyl group (e.g., also referred to as a "carbamate"). Furthermore, aminocarbonylamino groups (e.g., ureas) are also included as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. groups.

The term "interfacial area" as used herein refers to the true surface area of the surface, e.g., it does include the increased contact surface area resulting from the protrusions.

As used herein, the term "pharmaceutical compounds" includes "bioactive agents" and specific approved drugs. As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti- or pro-angiogenic factors, anti- or pro-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug.

A more complete listing of examples of pharmaceutical compounds (e.g., bioactive agents and specific drugs) suitable for use in various embodiments of the present inventions may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 14$^{th}$ ed. (November 2006), and the United States Pharmacopeia-25/National Formulary-20, published by the United States Pharmcopeial Convention, Inc., Rockville Md., 2001, the entire contents of which are herein incorporated by reference.

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

As used herein, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://tirrell-lab.caltech.edu/Research, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In some embodiments, the modifications of the peptide lead to a more stable peptide (e.g., greater half-life in vivo). These modifications may include cyclization of the peptide, the incorporation of D-amino acids, etc.

The term "projected area" as used herein refers to the overall macroscopic area of a surface and does not account for increased surface area due to surface roughness (e.g., due to protrusions).

BRIEF DESCRIPTION OF DRAWINGS

FIG. 1 is a perspective view of an embodiment of an adhesive article.

FIGS. 2A, 2B, 2C, 2D, and 2E are illustrations of embodiments of protrusions.

FIG. 3 is a cross-sectional diagram of protrusions.

FIG. 7D depicts adhesion trends of protrusions having configurations and dimensional parameters as shown in FIG. 7A, where pattern "Flat" refers to a surface substantially without protrusions. Pattern S1 refers to configuration 1 in FIG. 7A, pattern S2 refers to configuration 2 in FIG. 7A, and so on.

FIG. 9B provides data for a 0.3 degree of acrylation PGSA with 5% PEG (PGSA DA=0.3 with 5% PEGDA); and FIG. 9C provides data for a 0.3 degree of acrylation PGSA (PGSA DA=0.3).

FIG. 11A presents weight loss measurements after one week of implantation of samples with different compositions of PGSA polymer and a control of polyurethane (PU), which is a biocompatible polymer. Error bars represent one standard deviation.

FIG. 11B presents adhesion strength measurements of DXTA-coated PGSA DA=0.8 samples that were implanted for 48 hours in vivo. Error bars represent one standard deviation.

FIGS. 11C and 11D present data on tissue responses to microstructured PGSA DA=0.8 disks, subcutaneously implanted in the rat dorsum. Low magnification photomicrographs of hematoxylin and eosin (FIG. 11C) and Masson's trichrome (FIG. 10D) stained tissue sections are immediately adjacent to the PGSA implants. PGSA implants formerly occupied open spaces denoted by *. Nanotopography was placed next to muscle tissue (down), and samples were harvested after one week implantation. A mild response was observed with a thin inflammatory infiltrate without collagen deposition. Scale bar=400 micrometers.

FIGS. 11E, 11F, 11G, and 11H present data on tissue responses to patterned PGS disks, as a function of acrylation and PEG levels, subcutaneously implanted in the rat dorsum. High magnification photomicrographs of hematoxylin and eosin stained tissue sections are immediately adjacent to PGSA implants with DA=0.3 (FIG. 11E), DA=0.3 with 5% PEG DA (FIG. 11F), and DA=0.8 (FIG. 11G) as well as unpatterned polyurethane implants (FIG. 11H). PGS implants formerly occupied the open spaces denoted by *. Nanotopography was placed next to muscle tissue (down), and samples were harvested after one week implantation. The tissue responses were mild in all PGS implantation but more pronounced in the polyurethane implantation. Scale bar=100 micrometers.

DETAILED DESCRIPTION OF EMBODIMENTS

Adhesive Articles

Figure 4:
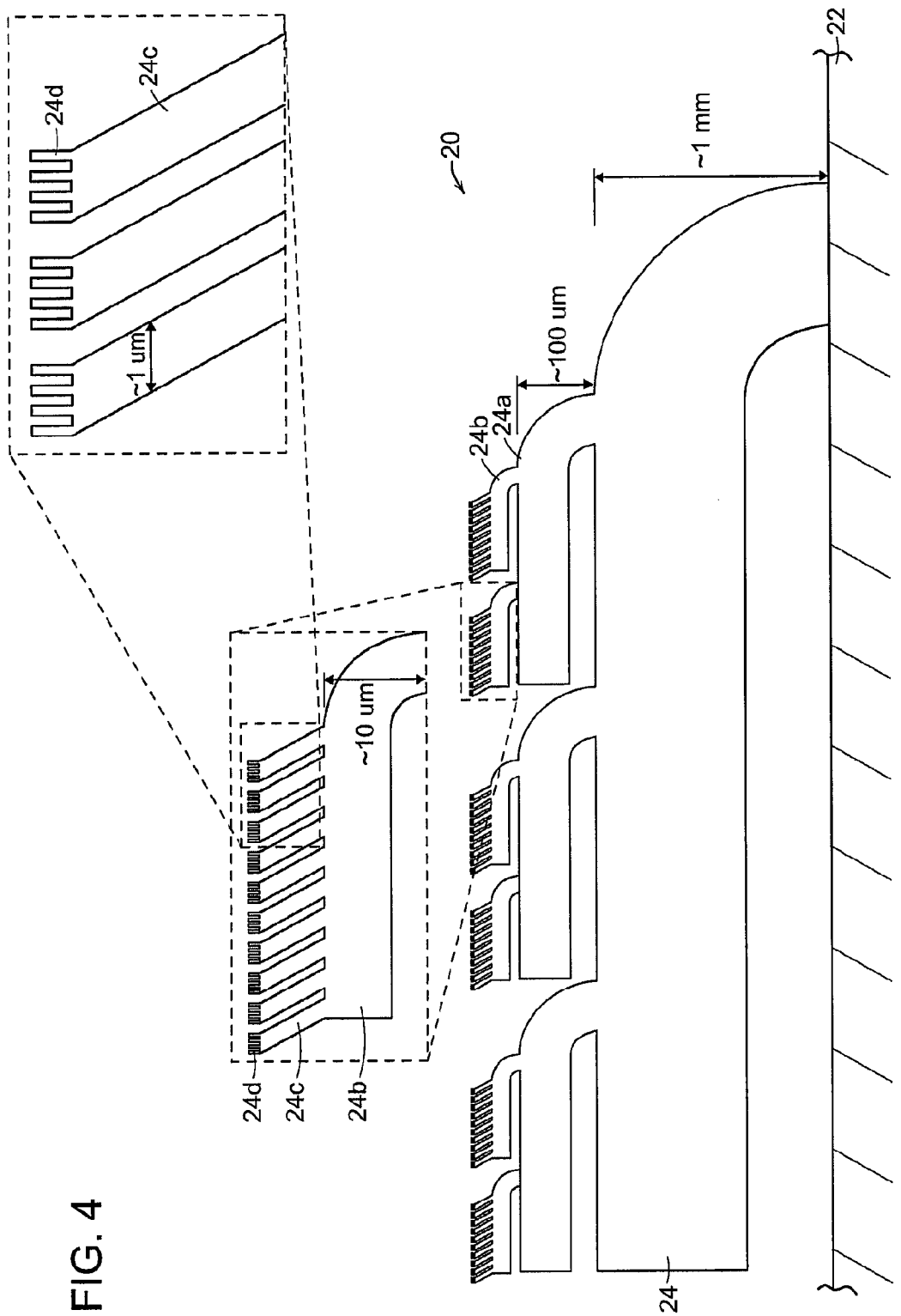
FIG. 4 is a detailed illustration of an embodiment of an adhesive article.

FIG. 1 shows an adhesive article 20 for adhesion to a biological tissue surface including a biocompatible and biodegradable substrate 22, and a plurality of protrusions 24 extending from the substrate. As shown, adhesive article 20 further includes a surface modification 26 on substrate 22 and protrusions 24 that enhances adhesion of the article to an applied surface. For example, surface modification can provide adhesive article 20 with a wet adhesive strength (e.g., in water or to a wet applied surface) that is greater than a dry adhesive strength (e.g., in air or to an applied surface free of water). In some embodiments, adhesive article 20 is substantially free of surface modification 26. As described more below, adhesive article 20 can be used in a variety of applications, such as medical applications (e.g., to join tissue and/or to deliver pharmaceutical compounds).

Substrate 20 can include (e.g., be formed solely of) a biocompatible and biodegradable material, such as those that breakdown to product(s) that are biocompatible and/or bioabsorbable. In some embodiments, substrate 20 and/or adhesive article 20 is degradable in vivo within the range of from approximately 1 day to approximately 1 year (e.g., less than approximately 60 days). In some embodiments, substrate 20 includes a material that is flexible and conformable. As a result, adhesive article 20 can conform to an applied surface, e.g., can conform to and be wrapped around an irregular tissue surface. Examples of materials for substrate 20 include polymers, such as, but are not limited to, poly(glycerol sebacate) (PGS), poly(glycerol sebacate acrylate) (PGSA), poly(lactic-co-glycolic acid) (PLGA), polycaprolactone (PCL), polyglycolide (PGA), polylactic acid (PLA), poly-3-hydroxybutyrate (PHB), star-poly-caprolactone-co-D,L-lactide, poly(tri-methyl carbonate-co-caprolactone), poly(ethylene glycol) (PEG), polyurethane, parylene-C, poly(citric-diol), hyaluronic acid, dextran, chitosan, alginate, keratin, carbon nanotubes, and/or agarose. Substrate 22 can include more than one materials (e.g., polymers) or compositions. For example, multiple compositions can be used to provide substrate 22 with anisotropic properties (e.g., materials with different degradation rates can be used to provide different rates along different directions of the substrate). The materials or compositions can be included as a mixture or as discrete portions (e.g., layers of different compositions). As an example, substrate 22 can include inorganic material(s), such as calcium phosphates, to alter mechanical properties, degradation, and/or adhesion. In some embodiments, adhesive article 20 includes a mucoadhesive material, such as, e.g., chitosan or alginate, to tailor adhesion of the article to mucous membranes that line various tissues, for example, in the oral cavity and gastrointestinal tract. The mucoadhesive material can be included in substrate 22 and/or protrusions 24.

The shape and size of substrate 22 can vary, as a function of the intended application of adhesive article 20. For example, to ease wrapping of adhesive article 20 around certain tissues (e.g., an intestinal tract), substrate 22 can be in the shape of a tape, which has a length substantially larger than its width. As another example, substrate 22 can be in the shape of a patch (e.g., greater than two inches in width) to facilitate wound closure. The thickness of substrate 22 can range, for example, from approximately 200 nm to approximately 2 cm. Thicker substrates 22 can provide adhesive article 20 with greater strength, and thinner substrates can provide the article with greater conformability. In some embodiments, adhesive article 20 has a substrate of different thicknesses or materials. For example, at the periphery of an adhesive article, the thickness of the substrate can be greater than the thickness at the inner portion of the article to provide a balance of strength and conformability. Differing thicknesses can also be used to control the time it takes for certain portions to degrade completely. In embodiments in which substrate 22 has different thicknesses, the range of thicknesses indicated above refers to an average thickness.

Similar to substrate 22, protrusions 24 can have a variety of shapes and sizes. As some examples, FIGS. 2A-2E show protrusions having the shape of a cone with a pointed tip (FIG. 2A), the shape of a round cylinder (FIG. 2B), the shape of a frustrum of a cone (FIG. 2C), the shape of a prism having a polygonal cross section (FIG. 2D), and the shape of a truncated, four-sided pyramid (FIG. 2E). The cross section of the polygonal prism can be regular or irregular, and can have three, four, five, six or more sides. Other shapes for protrusions 24 include regular or irregular pyramids having three sides, five sides, or six or more sides. The pyramids (e.g., FIG. 2E) can have pointed tips (e.g., as in FIG. 2A) or truncated, flat tips (e.g., as in FIGS. 2B and 2C). Referring to FIG. 2A, the angle (θ) between the surface of substrate 22 and the side of a protrusion 26 can range from approximately 0° to approximately 180°. Adhesive article 20 can include protrusions 24 of the same shape or different shapes, in any combination, depending on the intended application (e.g., desired degree of adhesiveness).

Referring to FIG. 3, and as illustrated in the following Examples, protrusions 24 can have various dimensions that affect the adhesive strength of adhesive article 20. In some embodiments, a protrusion 24 has an average height (H), as measured from the surface of substrate 22 to the tip of the protrusion, that ranges from approximately 0.25 micrometer to approximately 10 micrometers (e.g., from approximately 0.25 micrometer to approximately 5 micrometers, from approximately 0.25 micrometer to approximately 2.5 micrometers, from approximately 0.25 micrometer to approximately 1.5 micrometer). A protrusion 24 can have an average base width (B), as measured at the surface of substrate 22, that ranges from approximately 0.05 micrometer to approximately 10 micrometers (e.g., from approximately 0.05 micrometer to approximately 5 micrometers, from approximately 0.2 micrometer to approximately 2.5 micrometers, from approximately 0.2 micrometer to approximately 1 micrometer). The average tip width (T) of a protrusion 24 can range from approximately 0.05 micrometer to approximately 10 micrometers (e.g., from approximately 0.05 micrometer to approximately 5 micrometers, from approximately 0.1 micrometer to approximately 1 micrometers, from approximately 0.1 micrometer to approximately 0.5 micrometer). For pointed-tipped protrusions (e.g., FIG. 2A), the tip width (T) can be less than approximately 0.2 micrometer (e.g. less than approximately 0.05 micrometer). The average distance between juxtaposed protrusions, expressed as the center-to-center distance or pitch (P), can range from approximately 0.2 micrometer to approximately 100 micrometers (e.g., from approximately 0.2 micrometer to approximately 10 micrometers, from approximately 1 micrometer to approximately 5 micrometers, from approximately 1 micrometer to approximately 2 micrometers). Adhesive article 20 can include protrusions 24 of the same dimensions or different dimensions, in any combination, depending on the intended application (e.g., desired degree of adhesiveness).

In some embodiments, the dimensions of protrusions 24 are related. Some of these relationships, as illustrated in the Examples below, can enhance adhesion of article 20. For example, protrusions 24 can have an average height to base width ratio (H/B) in the range of from approximately 1:2 to approximately 10:1 (e.g., from approximately 2:1 to approximately 10:1; or from approximately 2:1 to from approximately 4:1). As another example, protrusions 24 can have a base width to tip width ratio (B/T) in the range of from approximately 2:1 to approximately 20:1 (e.g., from approximately 4:1 to approximately 10:1; or from approximately 2:1 to approximately 5:1). The tip width to pitch ratio (T/P) can range from approximately 0.8 to approximately 0.1 (e.g., from approximately 0.6 to approximately 0.2). These relationships indicate that, for example, one method to control the degree the adhesion based on geometry is by changing the ratios between tip diameter, base diameter and/or pitch.

Protrusions 24 can be arranged in various patterns and have various densities. In some embodiments, the density of protrusions 24, or the number of protrusions per unit area, ranges from approximately 10 protrusions/cm$^2$ to approximately $1 \times 10^{10}$ protrusions/cm$^2$ (e.g., from approximately 10 protrusions/cm$^2$ to approximately $1 \times 10^8$ protrusions/cm$^2$, from approximately $1 \times 10^3$ protrusions/cm$^2$ to approximately $1 \times 10^8$ protrusions/cm$^2$, from approximately $1 \times 10^3$ protrusions/cm$^2$ to approximately $1 \times 10^6$ protrusions/cm$^2$). Protrusions 24 can be regularly arranged, for example, in a hexagonal pattern, a square pattern, or a rectangular pattern. In some embodiments, protrusions 24 are irregularly or randomly arranged on substrate 22. Adhesive article 20 can include protrusions 24 arranged in the same pattern or different patterns, in any combination, depending on the intended application (e.g., desired degree of adhesiveness). Similarly, the density of protrusions 24 on substrate 22 can be substantially constant, or adhesive article 20 can have areas of different densities of the protrusions.

Protrusions 24 can include (e.g., be formed solely of) the same composition(s) as included in substrate 22, but in other embodiments, the protrusions can include one or more different compositions to create multi-component adhesive articles. As an example, protrusions 24 can include a composition that is stiffer or harder than a composition include in substrate 22. The stiffer composition can allow protrusions 24 to more easily penetrate an application site (e.g., tissue), thereby increasing contact area and adhesion. At the same time, the less stiff composition allows substrate 22 to be flexible and easily conformable to the application surface. As another example, article 20 can include protrusions including a first composition, a thin (e.g., approximately 1 micrometer to approximately 100 micrometers, or approximately 0.5 micrometer to approximately 5 micrometers) layer beneath the protrusions including the first composition, and a substrate including a second composition different from the first composition (e.g., to provide different stiffness). In some embodiments, protrusions 24 and substrate 22 can include compositions with different degradation rates, which can affect delivery of a pharmaceutical compound, if applicable. For example, one portion of an adhesive article can biodegrade quickly to provide a bolus delivery of a drug, and another portion of the adhesive article can biodegrade relatively slowly to provide an extended release of the drug. Such compositions and/or the geometry of protrusions 24 can be anisotropic. In certain embodiments, protrusions 24 have lower degradation rates than substrate 22 so the protrusions do not degrade quickly, e.g., due to their smaller dimensions and/or compositions.

In addition, protrusions 24 can include portions of different compositions. Similar to substrate 22, multiple compositions can be used to provide protrusions 24 with anisotropic properties (e.g., materials with different degradation rates can be used to provide different rates along different directions of a protrusion). The materials or compositions can be included as a mixture or as discrete portions (e.g., layers of different compositions).

In some embodiments, substrate 22 and/or protrusions 24 are porous. Porosity can enhance in-growth of tissue into adhesive article 20 and enhance securement of the article to the tissue (e.g., by acting as a mechanical interlock). Porosity can also be selected to control the biodegradation of adhesive article 20 and/or the delivery of a pharmaceutical compound, for example. In some embodiments, substrate 22 and/or protrusions 24 have a porosity of greater than approximately 20% (e.g., greater than approximately 40%, greater than approximately 60%, or greater than approximately 80%). Alternatively or additionally, substrate 22 and/or protrusions 24 have an average pore size of from approximately 10 nm to approximately 1 micrometer.

While protrusions 24 are shown above as extending from one plane (e.g., the surface of substrate 22), in other embodiments, the protrusions extend from multiple different planes. FIG. 4 shows an adhesive article 20' having a first set of protrusions 24 (only one protrusion 24 is shown for clarity) extending from substrate 22. Adhesive article 20' further includes a second set of protrusions 24a extending from a protrusion 24, a third set of protrusions 24b extending from a protrusion 24a, a fourth set of protrusions 24c extending from a protrusion 24b, and a fifth set of protrusions 24d extending from a protrusion 24c. As shown, in some embodiments, each set of protrusions 24, 24a, 24b, 24c and 24d is also smaller than the set of protrusions from which it extends. Each set of protrusions 24, 24a, 24b, 24c and 24d also extends from different planes than the other sets. As a result, adhesive article 20' has a multi-scale compliant structure, or a structure that has multiple levels of compliance that can allow the adhesive article to conform to surfaces or tissues that exhibit roughness on multiple length scales. In other words, adhesive article 20' has structures that can move up and down (relative to the surface of substrate 22) in response to a topographic variations of a surface (e.g., tissue), and these structures can be nested to provide compliance on multiple length scales (e.g., from sub-micrometer to hundreds of micrometers). Without being bound by theory, it is believed that this type of structure mimics the branched structure found on a gecko's foot and provides a similar benefit (e.g., conformability and adhesiveness).

Still referring to FIG. 4, the multi-scale compliant structure can be varied in other embodiments. For example, while article 20' includes five sets of protrusions 24, 24a, 24b, 24c and 24d, in other embodiments, the article includes two sets of protrusions, three sets of protrusions, four sets of protrusions, or six or more sets of protrusions. Furthermore, the sets of protrusions can be the same or different (e.g., in terms of compositions, dimensions, dimensional ratio (e.g., B/T), properties, such as degradation rates, etc). Some protrusions may not have any protrusions extending from them, while other protrusions in the same set (e.g., same plane) have protrusions extending from them. The geometries, arrangements and compositions of the sets of protrusions can independently varied as described herein for substrate 22 and protrusions 24. For example, a first set of protrusions may have a first shape (e.g., cylindrical or others shown in FIGS. 2A-2E) and include a first composition, and a second set of protrusions may be a second shape (e.g., non-cylindrical or others shown in FIGS. 2a-2E) and/or include a second composition.

Referring again to FIG. 1, surface modification 26 is provided to enhance the adhesiveness of adhesive article 20, e.g., relative an adhesive article without the surface modification. Surface modification 26 can also maintain a barrier for tissue-tissue adhesion or for tissue-device adhesion. Surface modification 26 can be on substrate 22 only, on selected protrusions 24 (e.g., on all the protrusions), or on both the substrate and selected protrusions. In some embodiments, surface modification 26 provides one or more of: (a) a functionalization of the surface of substrate 22 (e.g., by chemical reaction to provide aldehyde functional groups); and/or (b) addition of an adherent layer including a moiety capable of bonding to a biological tissue. For example, surface modification 26 can render the surface of substrate 22 and/or protrusions 24 capable of covalently bonding to the biological tissue, e.g., via covalent bonding of aldehyde functional groups to amine groups on the biological tissue surface. As other examples, surface modification 26 can include one or more of the following functional groups: a carbonyl, an aldehyde, an acrylate, a cyanoacrylate, and/or an oxirane. In some embodiments, surface modification 26 includes an layer of adherent present in an amount less than approximately 20 nanomoles per square centimeter of projected area (e.g., from approximately 1 nanomole to approximately 20 nanomoles per square centimeter of projected area).

Alternatively or additionally to surface modification 26, in some embodiments, a light permeable (e.g., translucent) adhesive article includes a pre-polymer as an additional glue. For example, a small amount of the pre-polymer can be applied between an intended application site (e.g., tissue) and the surface of substrate 22 and/or protrusions 24 to enhance intimate contact between the site and adhesive article 20. The pre-polymer can then be cured (e.g., photochemically) after adhesive article 20 has been applied, to adhere the article to the site. The pre-polymer can include the same material(s) used to form substrate 22 or different material(s).

Alternatively or additionally to surface modification 26, in some embodiments, biomolecules and/or bioactive agents are incorporated into substrate 22, protrusions 24, and/or an adherent layer on adhesive article 20, for example, using covalent and/or non-covalent interactions. Exemplary non-covalent interactions include hydrogen bonds, electrostatic interactions, hydrophobic interactions, and van der Waals interactions. The biomolecules can be used, for example, to recruit cells to a wound site and/or to promote a selected metabolic and/or proliferative behavior in cells that are at the site and/or seeded in substrate 22 and/or an adherent layer on adhesive article 20 (described below). Examples of biomolecules include growth factors or ligands such as, without limitation, transforming growth factor beta (TGF-β), acidic fibroblast growth factor, basic fibroblast growth factor, epidermal growth factor, insulin growth factor I and II (IGF-I and II), vascular endothelial-derived growth factor, bone morphogenetic proteins, platelet-derived growth factor, heparin-binding growth factor, hematopoetic growth factor, and peptide growth factor. In certain embodiments, integrins and cell adhesion sequences (e.g., the RGD sequence) are attached to substrate 22 and/or the adherent layer on adhesive article 20 to facilitate cell adhesion. Extracellular matrix components, e.g., collagen, fibronectin, laminin, elastin, etc., can also be combined with substrate 22 and/or an adherent layer on adhesive article 20 to manipulate cell recruitment, migration, and metabolism, and the degradation and mechanical properties of the material. In some embodiments, proteoglycans and glycosaminoglycans are covalently or non-covalently attached to substrate 22 and/or an adherent layer of adhesive article 20.

As indicated above, substrate 22 and/or an adherent layer on adhesive article 20 can be seeded with a variety of cells. For example, the cells can be delivered by adhesive article 20 for tissue regeneration. The cells can also facilitate remodeling of adhesive article 20 into new tissue. In some embodiments, the cells can deliver (e.g., secrete) a drug or a factor that has a therapeutic effect. Examples of cells include keratinocytes, fibroblasts, ligament cells, endothelial cells, epithelial cells, muscle cells, nerve cells, kidney cells, bladder cells, intestinal cells, chondrocytes, bone-forming cells, and/or stem cells, such as human embryonic or adult stem cells or mesenchymal stem cells.

Alternatively or additionally to surface modification 26, in some embodiments, one or more sacrificial layers are used to provide adhesive articles 20 that can be adjusted or re-positioned before the adhesive article completely adheres to its intended surface (e.g., tissue). The sacrificial layers are removed from the surface of substrate 22 and/or protrusions 24 before adhesive article 20 is completely adhered to the application site. Chemical and/or physical interactions with tissue can be one mechanism through which a sacrificial layer is removed from the surface of adhesive article 20. For example, the sacrificial layer can include a salt coating or barrier that slowly dissolves when applied to tissue. The slow dissolution provides the user time to re-adjust or re-position adhesive article 20 before the article adheres too strongly to the tissue. Other methods through which the sacrificial layer can be removed include, but are not limited to, light, pH, temperature, sound and/or physical mechanisms. As another example, adhesive article 20 can include pressure-sensitive particles that contain a release agent (e.g., biomolecules). After adhesive article 20 is correctly positioned (e.g., on tissue), sufficient pressure (or another mechanism to activate adhesion such as temperature change) can be applied to release the release agent and/or achieve adhesion. Alternatively or additionally to being on adhesive article 20, the sacrificial layer can be applied to the application site (e.g., tissue) prior to contacting the adhesive article to the site.

In other embodiments, the sacrificial layer is engineered to stay at an applied adhesion site and to degrade over a selected time period after adhesive article 20 is removed from the adhesion site. For example, patterns resulting from contact of adhesive article 20 containing the sacrificial layer can remain on the contacting tissue surface after article 20 is removed. These patterns can, for example, provide sites for cell attachment or localized points of adhesion and/or visible marks for surgical applications.

In some embodiments, adhesive article 20 can be removed by a release agent including a mildly basic solution with a pH higher or lower than 7 or by light. Alternatively or additionally, adhesive article 20 can be removed by a release agent including an esterase enzyme, such as cholesterol esterase (Nijst et al., Biomacromolecules 2007, 8, 3067). Such release agents can be useful when adhesive article 20 is removed from the tissue, and a new adhesive can be applied, and/or to remove the adhesive article 20 after its intended use is fulfilled.

In some embodiments, at least a portion of adhesive article 20 capable of covalently bonding to a biological tissue has an interfacial surface area that is approximately 1.2 times greater than the projected surface area of the portion. For example, as protrusions 24 are pushed into tissue, the sides of the protrusions and the areas between the protrusions can increase the surface area that contacts the tissue (e.g., compared to only the tips of the protrusions). This increased contact area can enhance adhesion of adhesive article 20 to the tissue. In some embodiments, protrusions 24 can penetrate into tissue, thereby further increasing contact area and adhesion.

Covalent bonding of adhesive article 20 to a biological tissue can be reversed by application of a biodegradable and biocompatible release agent (e.g., a drug, protein, peptide, suspended particle, DNA, and RNA). For example, the release agent can be active when the tissue has developed the correct geometry or connectivity at the interface with adhesive article 20, at which time the release agent is activated.

Fabrication of Adhesive Articles

Adhesive article 20 can be fabricated with a variety of techniques. Exemplary techniques include contact lithography, nanodrawing, photolithography followed by etching or nanomolding, nanocasting using vertically aligned multi-walled carbon nanotubes. See, e.g., Geim A K, Dubonos S V, Grigorieva I V, Novoselov K S, Zhukov A A, Shapoval S Y. Microfabricated adhesive mimicking gecko foot-hair. *Nat Mater* 2003; 2(7):461-3; eong H E, Lee S H, Kim P, Suh K Y. Stretched Polymer Nanohairs by Nanodrawing. *Nano Letters* 2006; 6(7):1508-1513; and Yurdumakan B, Raravikar N R, Ajayan P M, Dhinojwala A. Synthetic gecko foot-hairs from multiwalled carbon nanotubes. *Chem. Commun.* (Camb) 2005(30):3799-801. In various embodiments, fabrication methods avoid high temperatures and/or harsh chemical modifications.

Figure 5:
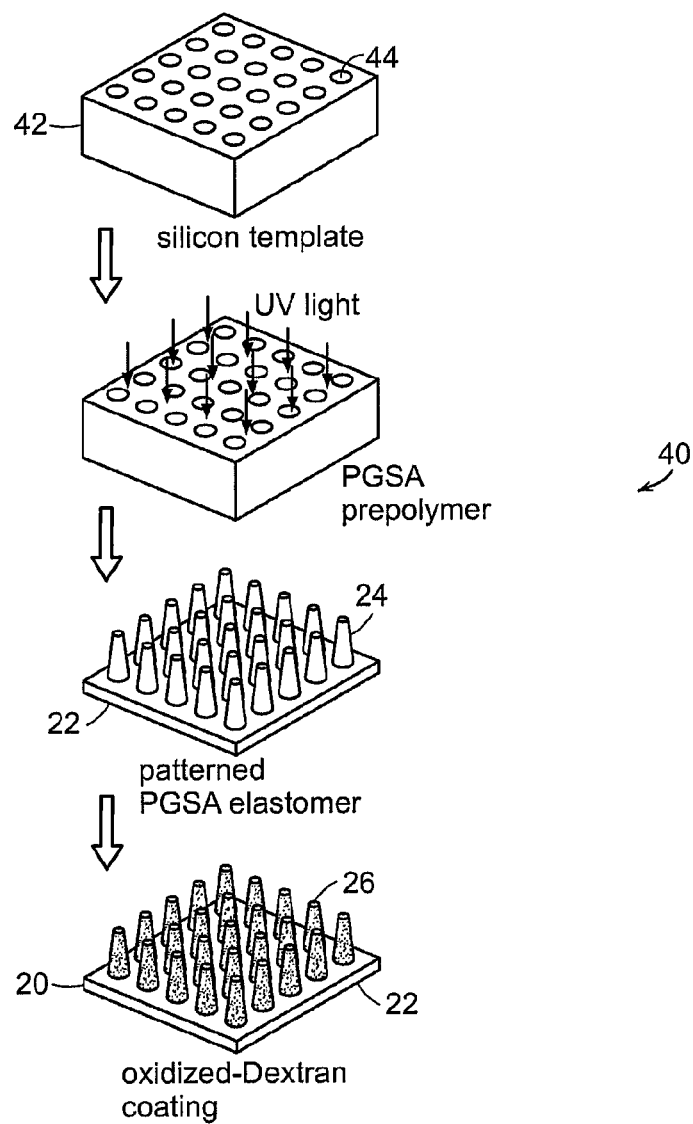
FIG. 5 is a diagram illustrating an embodiment of a method of making an adhesive article.

FIG. 5 shows an embodiment of a method 40 for fabricating adhesive article 20. As shown, a template 42 (e.g., a silicon template) is prepared using, for example, a combination of photolithography followed by reactive ion etching (RIE). Template 42 includes a plurality of mold cavities 44 having the shape(s), patterning(s) and dimensions of protrusions 24, or shapes that give rise to protrusions 24. Next, the material(s) (e.g., PGSA polymer) for protrusions 24 and substrate 22 is filled into cavities 44 and placed on template 42. In some embodiments, no high vacuums are used to fill cavities 44, but in other embodiments, vacuums and/or temperature variations are used to fill the cavities. Then, the material(s) for protrusions 24 and substrate is cured, for example, using ultraviolet radiation in minutes at room temperature. The cured material(s) is then separated from template 42 to provide an uncoated adhesive article 20.

To fabricate complex structures (e.g., such as that shown in FIG. 4), template 42 can have a photoresist patterned on top to form larger mold cavities. Multiple layers of photoresists can be patterned using spin-on and laminated resists for larger structures. To release the structures, the photoresists can be dissolved in a solvent.

In embodiments in which adhesive article 20 includes surface modification 26, the surface modification can be created on the surface of substrate 22 and/or protrusions 24 during the patterning process described above, after the patterning process, or both. For example, as part of the patterning process, the material(s) for surface modification 26 can be deposited in cavities 44 and/or on the surface of template 42 prior to filling the cavities and covering the template, and curing. As a specific example, a solution of dextran aldehyde (DXTA) in water can be spin coated on the surface of template 42 to cover the template and/or cavities 44. After drying, the material(s) for substrate 22 and protrusions 24 can be placed in cavities 44 and on template 42 and cured. As a result, DXTA molecules can be incorporated into the surface of the resulting pattern, both physically (e.g., as an interpenetrating network), as well as chemically (e.g., through formation of hemiacetal linkages).

Alternatively or additionally, surface modification 26 can be placed (e.g., coated) on the surface of substrate 22 and/or protrusions 24 after material (e.g., cured polymer) is separated from template 42. Methods of coating include, but are not limited to, spin-coating, Langmuir-Blodgett deposition, chemical vapor deposition (CVD), and self-assembling monolayers tailored to bind to either the material included in article 20 (e.g., for surface chemistry) or template 42 (e.g., for release).

In embodiments in which adhesive article 20 includes biomolecules, cells, an adherent layer, and/or a sacrificial layer, these materials can be incorporated similarly to how surface modification 26 is incorporated. Certain materials, for example, biomolecules and cells, can also be intimately mixed with the material (e.g., polymer(s)) used to form substrate 22 and/or protrusions 24.

Embodiments of fabricated adhesive article 20 have high adhesive strength, which, as used herein, refers to a macroscopic measurement. A variety of techniques to measure adhesive strength are known, including but not limited to, those measured according to ASTM standards D4501, D4541 and D6862-04. The adhesive strength can range from approximately 0.05 to approximately 50N/cm$^2$ of projected area. For example, of projected area, the adhesive strength can be greater than or equal to approximately 0.05 N/cm$^2$, approximately 0.5 N/cm$^2$, approximately 1 N/cm$^2$, approximately 5 N/cm$^2$, approximately 10 N/cm$^2$, approximately 15 N/cm$^2$, approximately 20 N/cm$^2$, approximately 25 N/cm$^2$, approximately 30 N/cm$^2$, or approximately 40 N/cm$^2$; and/or less than or equal to approximately 50 N/cm$^2$, approximately 40 N/cm$^2$, approximately 30 N/cm$^2$, approximately 25 N/cm$^2$, approximately 20 N/cm$^2$, approximately 15 N/cm$^2$, approximately 10 N/cm$^2$, approximately 5 N/cm$^2$, approximately 1 N/cm$^2$, or approximately 0.5 N/cm$^2$.

In some embodiments, adhesive article 20 has an adhesive strength of greater than approximately 0.5N/cm$^2$ of projected area and an adherent layer amount of less than approximately 20 nanomoles per square centimeter of projected area.

In certain embodiments, adhesive article 20 has a wet adhesive strength that is greater than a dry adhesive strength. For example, the wet adhesive strength (e.g., when contacting water (e.g. in vivo)) can be greater than approximately 0.1 Newtons per square centimeter of projected area, and the dry adhesive strength (e.g., when not contacting water (e.g., against a dry surface, such as, e.g., a glass, a silicone-containing material)) can be less than about 0.01 Newtons per square centimeter of projected area.

Embodiments of adhesive article 20 can also exhibit a high tensile Young's modulus, maximum elongation, swelling in water, and/or crosslinking density. As used herein, tensile Young's modulus and maximum elongation are determined using ASTM standard D412-98a. In some embodiments, the tensile Young's modulus ranges from approximately 0.05 MPa to approximately 17 MPa. The tensile Young's modulus can be greater than or equal to approximately 0.05 MPa, approximately 1 MPa, approximately 3 MPa, approximately 5 MPa, approximately 10 MPa, or approximately 15 MPa; and/or less than or equal to approximately 17 MPa, approximately 15 MPa, approximately 10 MPa, approximately 5 MPa, approximately 3 MPa, or approximately 1 MPa. The maximum elongation can be greater than approximately 20% (e.g., greater than approximately 40%, greater than approximately 60%, greater than approximately 80%, greater than approximately 100%, or greater than approximately 160%). The degree of swelling in water can range from approximately 0% to approximately 100%. For example, the degree of swelling can be greater than or equal to approximately 0%, approximately 5%, approximately 10%, approximately 15%, approximately 20%, approximately 40%, approximately 60%, or approximately 80%; and/or less than or equal to approximately 100%, approximately 80%, approximately 60%, approximately 40%, or approximately 20%, approximately 15%, approximately 10%, or approximately 5%.

As some specific examples, adhesive article 20 can have one or more of the following properties: (a) a tensile Young's modulus less than approximately 17 MPa; (b) a tensile Young's modulus greater than approximately 0.5 MPa; (c) a tensile Young's modulus greater than approximately 0.6 MPa and an elongation of greater than approximately 20%; (d) a tensile Young's modulus greater than approximately 0.25 MPa and a swelling in water of greater approximately about 1%; (e) a tensile Young's modulus greater than approximately 0.25 MPa and a swelling in water of greater than approximately 20%; (f) a tensile Young's modulus greater than approximately 0.25 MPa and a swelling in water of greater than approximately 40%; (g) a tensile Young's modulus greater than approximately 0.25 MPa and a swelling in water of greater than approximately 80%; (h) a Young's modulus in the range between approximately 0.4 MPa and approximately 0.55 MPa; (i) a maximum elongation greater than approximately 60%; (j) a maximum elongation greater than approximately 100%; (k) a maximum elongation greater than approximately 160%; (l) DA from approximately 0.25 to approximately 0.35, and a Young's modulus in the range of from approximately 0.6 to approximately 1.0 MPa; (m) DA from approximately 0.25 to approximately 0.5, and an elongation greater than approximately 40%; and (n) DA from approximately 0.25 to approximately 0.35, and a Young's modulus from approximately 0.6 to approximately 1.0 MPa, and a crosslink density from approximately 90 to approximately 120.

Applications

Adhesive article 20 described herein can be used in any application where adhesiveness is required or wanted. The surface(s) to which adhesive articles 20 are applied can be dry or wet (e.g., in an aqueous environment, such as biological tissue).

In some embodiments, adhesive article 20 is used in medical applications (e.g., as medical devices). More specifically, adhesive articles 20 can be used to join tissue (e.g., one or more tissue in vivo). Conformal sealing of damaged tissue can be challenging due to the requirement of good surface adhesion as well as shear strength during tension loading. For example, lung punctures, punctured blood vessels and anastomosis of the intestine can be challenging wounds to seal. Adhesive article 20 can be designed to match tissue mechanical properties to provide conformal wound closure and sealing. Such adhesive articles can be particularly useful in applications where there is considerable tissue movement. As another example, adhesive articles 20 can be used as surgical tape. A biocompatible, biodegradable surgical tape can be used, e.g., to stop bleeding during surgery but does not need to be removed before the surgeon sutures the wound closed. The tape can then biodegrade over time.

Figure 6A:
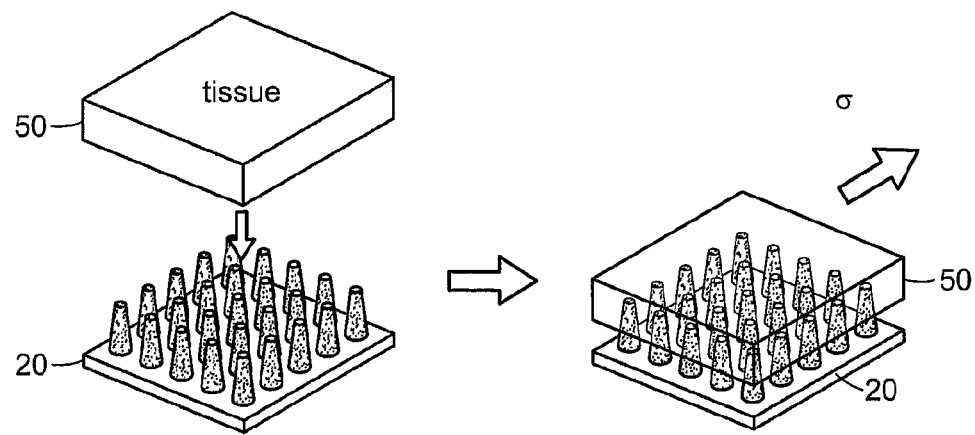
FIG. 6A illustrates mechanical interactions between an adhesive article and tissue.
Figure 6B:
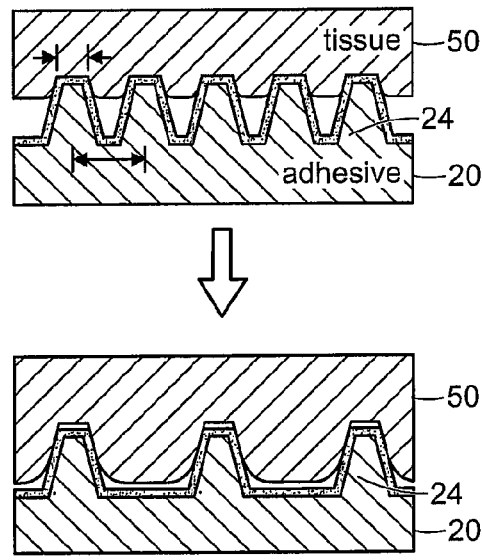
FIG. 6B illustrates conformability of tissue with the adhesive article.

As an example, FIGS. 6A and 6B illustrate the ability of adhesive article 20 to engage mechanically and to conform to tissue 50. More specifically, as adhesive article 20 is applied to tissue 50, the tissue can conform to the surfaces of protrusions 24 and substrate 22, thereby increasing contact area and adhesion between the adhesive article and the tissue. FIG. 6B further shows that decreasing the tip width to pitch ratio (T/P) can further increase contact area and conformability. In some embodiments, protrusions 24 (e.g., pointed tipped protrusions) penetrate into tissue 50 to anchor adhesive article 20 to the tissue. But regardless of whether protrusions 24 actually penetrate tissue 50 or not, as shown in FIGS. 6A and 6B, the protrusions, substrate 20 and the tissue mechanically interface and engage to provide a mechanical interlock that resists shearing between adhesive article 20 and the tissue.

In some embodiments, adhesive article 20 can be fabricated into a biodegradable stent. The stent can increase the diameter of a blood vessel to increase flow through the vessel, but since the stent is biodegradable, the blood vessel can increase in diameter with a reduced risk of thrombosis or covering the stent with scar tissue, which can re-narrow the blood vessel. The time a stent remains in place and retains its shape before degradation can vary from patient to patient and depend partially on the amount of blockage and the age of the patient (e.g., older patients may need more time to heal). In certain embodiments, adhesive articles 20 can cover an outer surface of a stent (with protrusions 24 extending outward) to help adhere the stent to a vessel wall in a manner that is less damaging to the tissue than an uncovered stent. Similarly, adhesive article 20 can cover the surface of devices which are in contact with tissue to provide a suitable interface that can be adhesive to tissue.

Numerous other applications are possible. For example, adhesive article 20 can be used to prevent air leaks following a lung resection; to reduce the time for surgical procedures (e.g., sutures may require aligning tissue with each stitch, but an adhesive tape may be able to align the tissue once); to seal dura; to ease laproscopic procedures (e.g., it can be difficult to tie knots in small spaces, but a tape can be rolled up and placed through a large bore needle or trocar, and unfolded on the surgical site); as a degradable skin adhesive (e.g., that can release agents as it degrades); as a hernia matrix to prevent or to reduce the need for stables or tacks; to prevent blood loss; to manipulate organs or tissues during surgical procedures (e.g., to push the liver aside and hold it in place); to secure corneal transplants in place; to patch a heart to deliver drugs and/or to reduce growth of the heart after myocardial infarction; to attach another material to a tissue (e.g., to enhance engraftment of graft tissue, or to bond a drug delivery device or scaffold or other construct to a tissue or organ); to augment sutures or staples; to distribute forces across tissue; to prevent leaks; as a barrier membrane on the skin to prevent evaporation of water from burnt skin; as a patch for delivery of anti-scar medication; to attached devices (e.g., drug delivery devices, sensors) to tissue; to attach devices (e.g., a drug delivery device) to mucus membrane (e.g, mouth, gut, anus, nostrils, vagina, etc); to prevent adhesion of brain tissue to the skull after brain surgery or implantation of devices; as adhesive barriers (as applies to surgical applications) for tissue-tissue adhesion and/or tissue-device adhesion; to prevent blood loss from blood vessels; as a tape to secure devices within an oral cavity, such as to hold dentures and oral appliances; as a tape to anchor soft tissue to bone; and to prevent peritoneal adhesion (e.g., where one side is adhesive and other is not). Adhesive article 20 can also be used to coat tools, such as surgical instruments (e.g., forceps, retractors), to enhance the ability of the tools to manipulate (e.g., grip) objects (e.g., tissue). Adhesive article 20 can also be used in industrial applications where it is useful to have a degradable adhesive that is biocompatible (e.g., to reduce potential toxicity of the degradation products, such as marine applications (e.g., underwater use, attach to surface of boats, etc).

In embodiments in which adhesive article 20 includes a biomolecule or a bioactive agent, the biomolecule or the bioactive agent can be locally delivered where the adhesive article is placed. Because adhesive article 20 can be elastic, it can conform to the application site and move with the patient as he/she walks, runs, sits, etc.

EXAMPLES

Other aspects and embodiments may be further understood in light of the following examples, which are not exhaustive and which should not be construed as limiting.

The adhesive articles of the following examples were fabricated and characterized substantially as follows.

Nano-molding of PGSA polymer

Templates (e g, nanomolds) were fabricated using photolithography followed by reactive ion etching of an oxide layer on a silicon wafer. Four-inch diameter silicon wafers were oxidized for 10 hours at 1100° C. in atmospheric pressure oxygen with a flow rate of 50 standard cubic centimeters per minute (sccm), and hydrogen (30 sccm) to grow an oxide layer of approximately two microns thick. Silicon wafers, each with a 10-micron thick oxide layer, were purchased from Silicon Quest International. The oxide layer thickness was measured with Filmetrics F20 and F50 spectral reflectometers. Each silicon wafer with an oxide layer was baked at 110° C. to dehydrate its surface and spin-coated with hexamethyldisilazane (HMDS) at 5000 rpm for 10 seconds to promote resist adhesion. A photoresist (Shipley 1805) was then spin-coated (EVG101) on the wafers at 3500 rpm for 20 seconds. The wafer was then softbaked on a hotplate at 115° C. for one minute to yield a resist film approximately 500 nm thick. The photomask was fabricated by Photronics Inc. Resist exposure was done with a Karl Suss MA-6 contact aligner with an exposure dose of 96 mJ/cm$^2$, and the resist was developed for 45 seconds in Shipley MF-319 developer followed by a three minute rinse in de-ionized (DI) water and spin drying. The wafer was then ashed in a March barrel asher for 30 seconds at 55 W in a 250 mTorr oxygen plasma. Reactive ion etching (RIE) was then used to transfer a pattern of hole arrays into the oxide layer to form the mold. A Surface Technology Systems (STS) Multiplex RIE was used with gas flows of 14.4 sccm of $CHF_3$ and 1.6 sccm of $CF_4$ at 20 mTorr pressure. An oxide etch rate of approximately 2.8 nm/second was achieved by using 200 Watts of RF power. Three mold depths were targeted by controlling the etch time, with approximate depths of 1 µm, 2 µm, and 3.5 µm. After etching, the resist layer was removed by sequential rinse in acetone and SVC-12 (Microchem) for 30 minutes each and EKC-270 stripper (DuPont) for 2.5 hours, followed by a 10 minute rinse with DI water and spin drying. The etched oxide depth was measured by profilometry on a Tencor Alpha-Step-IQ. To develop patterned polymer surfaces, PGSA pre-polymer was poured onto silicon molds without vacuuming the polymer, and UV cured as previously described. See Nijst C L, Bruggeman J P, Karp J M, Ferreira L, Zumbuehl A, Bettinger C J, Langer R. Synthesis and Characterization of Photocurable Elastomers from Poly(glycerol-co-sebacate). Biomacromolecules 2007; 8(10):3067-3073. The macroscopic film thicknesses for all the polymer adhesives were kept constant at 0.94 mm±0.03 mm.

Shear Adhesion Tests

Shear adhesion tests were performed on the polymer surfaces using an Electroforce ELF 3200 mechanical tester (Bose-Enduratec, Framingham, Mass.) controlled by Win-Test software (Ver. 2.51) using custom fabricated stainless steel tissue grips and a 250 g load cell (model 31-1435-03; Sensotech, Inc., Columbus, Ohio).

This test of shear resistance provides a measure of the ability of the patterns, once immobilized, to resist lateral movements on tissue. To test adhesion, 4-mm diameter discs of the patterned polymer were cut out of patterns using a dermal biopsy punch (Miltex Instrument, 33-35) and glued to a glass slide to provide a flat adhesive surface with well-defined area. Porcine intestine tissue was cut into 2 cm×2 cm square sections and glued to a glass slide using cyanoacrylate glue. The outer surface of the intestine tissue was used for adhesion tests. A patterned sample and a tissue slide were positioned parallel to provide contact between the tissue and the patterned polymer sample. The position of the test samples within the grips was substantially identical for all samples to minimize sample-to-sample variance in the initial contact or pre-load force. Upon initiation of the adhesion test, the tissue slide was displaced at 8 mm/min while the force was recorded. The maximum adhesion force was measured. For each sample, four tests were performed to obtain a statistical result. The tests conducted are substantially similar to those provided by standard ASTM D4501.

Synthesis and Characterization of Dextran-Aldehyde (DXTA)

An aqueous solution of dextran (from *Leuconostoc mesenteroides*; $M_w$ between 64,000 and 76,000 Da, Sigma) (10 g in 100 mL of distilled water) was oxidized with 3.3 g of sodium periodate (Sigma), at room temperature in the absence of light. The resulting solution was dialyzed for 3 days (molecular weight cut-off of 3,500 Da) and lyophilized thereafter. The isolated yield was 90%. The degree of oxidation (DO) of DXTA, defined as the number of oxidized residues per 100 glucose residues, was quantified using tert-butylcarbazate (tBC), as reported previously, and $^1$H NMR. DXTA solution was spin coated on the surfaces of the PGSA patterned samples using a speed of 4000 rpm which provided uniform surface coatings. Dextran aldehyde hydrogels have an elastic modulus between 20 kPa and 60 kPa, depending on the degree of crosslinking as described in Maia et al. (2005) Synthesis and characterization of new injectable and degradable dextran-based hydrogels. *Polymer* 46, 9604-9614.

Surface Analysis of Dextran Aldehyde at the Interface of Tissue and Polymer Using X-Ray Photo-Electron Spectroscopy (XPS) and Infrared Spectroscopy Analyses XPS measurements were performed on an Axis Ultra spectrometer (Kratos Analytical of Manchester, England) using Al $K_\alpha$ (1486.6 eV) radiation source (150 W). The operating pressure during analysis was in the low $10^{-9}$ Torr range. Survey spectra were collected over a range of 0-1100 eV with analyser pass energy of 100 eV. High-resolution C(1s) and O(1s) spectra were collected with an analyser pass energy of 20 eV. In both cases, an area of 0.3 mm$^2$ of the sample was examined, and atomic compositions were quantified using tabulated sensitivity factors. Angle-resolved analysis was performed at a takeoff angle of 70° Amine-coated microarray glass slides (Superamine2 from ArrayIt Inc.) with amine concentration of $2\times10^{13}$ units per mm$^2$ (as characterized by the supplier) were used for surface characterization to mimic amine moieties on the tissue surface.

Fourier transform infrared (FTIR) spectroscopy was performed using a Nicolet Magna 860 FTIR instrument. One hundred scans were performed with a resolution of 4 cm$^{-1}$. The spectra resulting from three different samples were normalized based on the absorbance at 2930 cm$^{-1}$ corresponding to the stretching of the C—H groups in the samples.

In Vivo Studies

Surgical Procedures

The animal care, anesthesia, and sacrifice protocols were similar for both the dorsal subcutaneous and subfascial implantation studies described below. Male Wistar rats weighing approximately 350 grams (Charles River Laboratories, Wilmington, Mass.) were acclimatized before surgery. Animals were anesthetized with Ketamine (75 mg/kg) and Dormitor (0.5 mg/kg) and recovered with Antisedan. After surgery, animals were housed in a temperature/humidity controlled environment with 12 hr light/dark cycles and had unrestricted access to water and standard rat food. Prior to sample harvest, the rats were sacrificed with an overdose of Pentobarbital. All surgical procedures were approved by the Institutional Care and Use Committee of the Massachusetts General Hospital and performed according to the NIH Guidelines for the Care and Use of Laboratory Animals.

Biocompatibility Studies

Tissue response was determined for patterned PGS materials (0.3 acrylation (DA) or DA=0.3; DA=0.3 with 5% polyethylene glycol diacrylate (PEGDA); and DA=0.8) as well as an un-patterned non-resorbable polyurethane (the control material). For each PGS formulation, 5-mm diameter disks were punched from polymer sheets of 1.1 mm thickness using dermal biopsy punches (Acuderm, Acu-Punch, Ft. Lauderdale, Fla.), dried at 60'C at 50 Torr for 48 hr, weighed, and disinfected by UV light.

The disks were subcutaneously implanted into pockets on the backs of five Wistar rats (n=8 for each PGS formulation; n=6 for polyurethane). After shaving and disinfection, a small incision was made in the dorsal midline of each animal. Six small subcutaneous pockets deep inside the loose areolar tissue were developed using blunt dissection: bilaterally over the scapular and the latissimus dorsi regions and caudal to the pelvic brim. One sterile PGS disk was inserted into each pocket, with the pattern facing the muscle, and each incision was closed with 2-0 silk sutures. One week after implantation, the rats were sacrificed, and samples were located by palpation. Each PGS disk was excised with all associated surrounding dermal and muscle tissues.

Functional Adhesion Studies

Tissue adhesion of dextran-coated, patterned, 0.8 acrylation PGS samples was evaluated in a subfascial environment. A small incision was made in the ventral midline of each animal (n=7). Dissection was carried down to the linea alba, and all loose areolar tissue was gently swept off the abdominal wall using damp gauze. After identifying the fascia, a small incision parallel to the linea alba was made bilaterally in the ventral aspect of the rectus sheath. A small fascial flap was developed using a blunt dissection technique on each side of the incision. A sample (1 cm×1 cm, 1.1 mm thick) was placed in each flap on the exposed underlying rectus muscle with the pattern oriented outward toward the fascia. One patterned/dextran-coated sample and one patterned/uncoated sample were inserted into each animal. The overlying tissues were re-approximated and the skin was closed with 2-0 silk sutures. The rats were sacrificed after 48 h for adhesive testing. After shaving, the entire abdominal wall was removed and the samples were identified by palpation. Each explant was excised from the abdominal wall with associated surrounding tissues from the dermis to the underlying muscle layer. Samples for adhesion testing were immersed in sterile saline and tested immediately after removal. The samples explanted at 7 d (n=3) were prepared for histologic analysis.

PGS Explant Sample Preparation

For weight loss, the PGSA explants were carefully dissected from surrounding tissue and rinsed in distilled water, dried at 60° C. for 48 hr at 50 Torr vacuum, and weighed. For histological evaluation, the tissue surrounding the implant was carefully trimmed (2×2×0.5 cm), and both the tissue and sample were fixed in 10% buffered formalin. After three days, the tissue samples were cut in half, the capsules were incised, and the polymer disks were removed. Tissue was cut into 3-mm wide sections and embedded in paraffin. Sections (6 μm thick) were stained with hematoxylin and eosin (H&E) and Masson's trichrome. H&E and Masson's trichrome stained tissue sections were analyzed for the degree of inflammation and fibrosis. The tissue response was characterized based on the level of neutrophils, lymphocytes, macrophages, and giant cells. Fibrosis was identified primarily by collagen deposition.

Example 1

Examples of Effects of Pattern Dimensions on Adhesive Properties

Examples of the effects of pattern dimensions on the adhesive properties of the PGSA elastomer are illustrated in FIGS. 7A-7D. Protrusions with tip diameters ranging from ~100 nm to 1 μm, and protrusion heights from ~0.8 μm to ~3 μm are illustrated (see, e.g., FIG. 7A). In these Examples, a square lattice surface packing of protrusions was used instead of a hexagonal lattice to facilitate reducing the probability of protrusion collapse. Protrusion collapse did not occur after removal of the pattern from the mold as verified by SEM.

These Examples present data for in vitro adhesion of the adhesive articles against wet tissue to mimic physiological conditions. Initially, in-vitro shear or sliding adhesion tests were used to determine the adhesion strength of the microstructured articles (without chemical surface modification) to porcine intestinal tissue. This test mimics potential shear forces that may be applied to the tissue adhesive after surgical placement. The maximum separation force was used as a descriptor of adhesion for all materials. Tissue adhesion of the patterns was normalized to adhesion strength of the flat polymer to allow comparison across different patterns. In comparison to the flat polymer, most of the patterned surfaces provided nearly a two-fold increase in tissue adhesion.

Figure 7A:
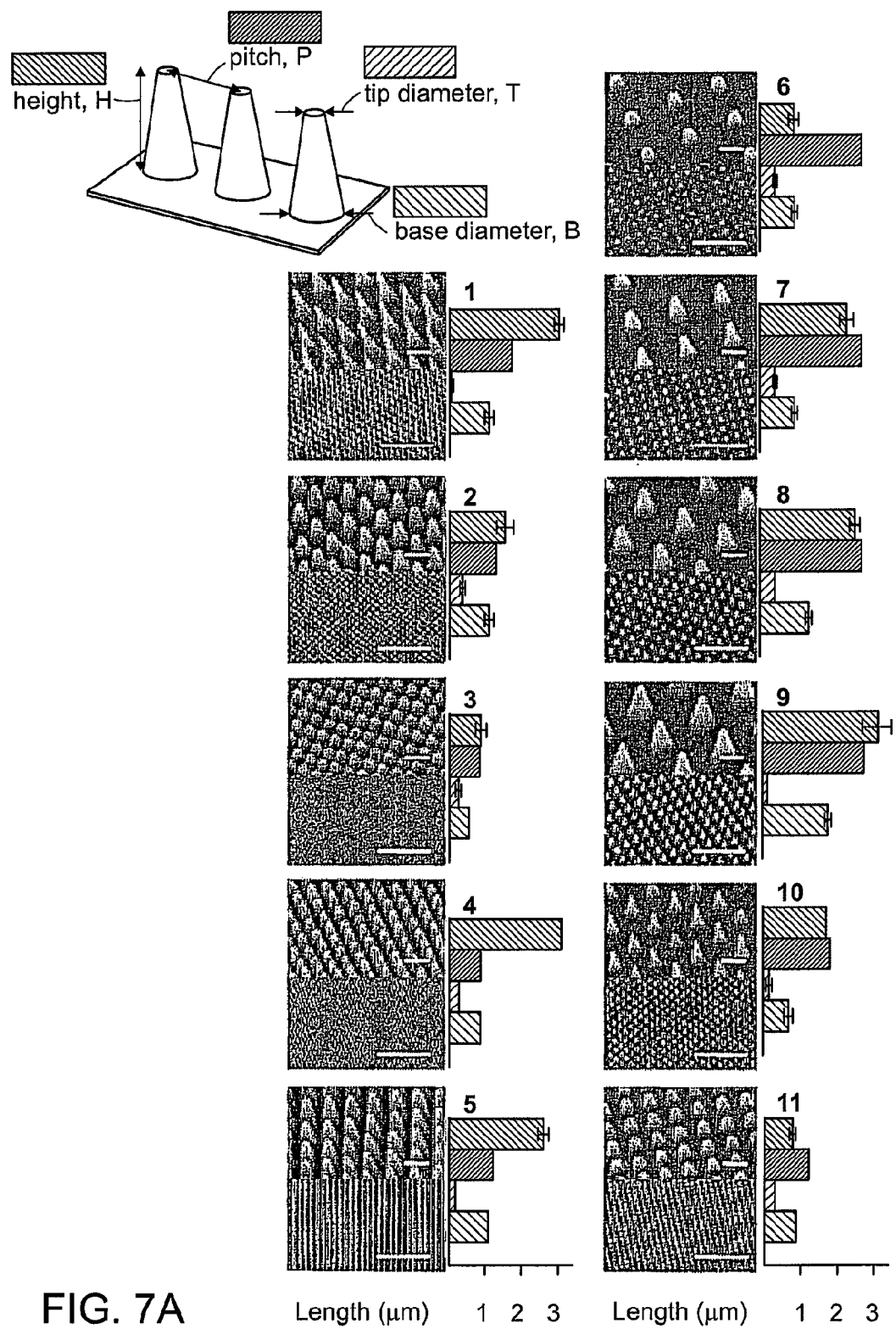
FIG. 7A show scanning electron microscopy (SEM) images of protrusions of various dimensional parameters. The small scale bar in the SEM images represents 1 micrometer, and the large scale bar represents 10 micrometers. To the right of each SEM image are four bars corresponding to various dimensional parameters. The uppermost bar indicates protrusion height (H); the next bar down indicates center-to-center pitch (P); the bar below that indicates tip width (T); and the bottom bar indicates base width (B). Good pattern fidelity is evident from the images taken at lower magnification. Protrusion dimensions were measured using optical profilometry. Error bars represent one standard deviation of measurements.
Figure 7B:
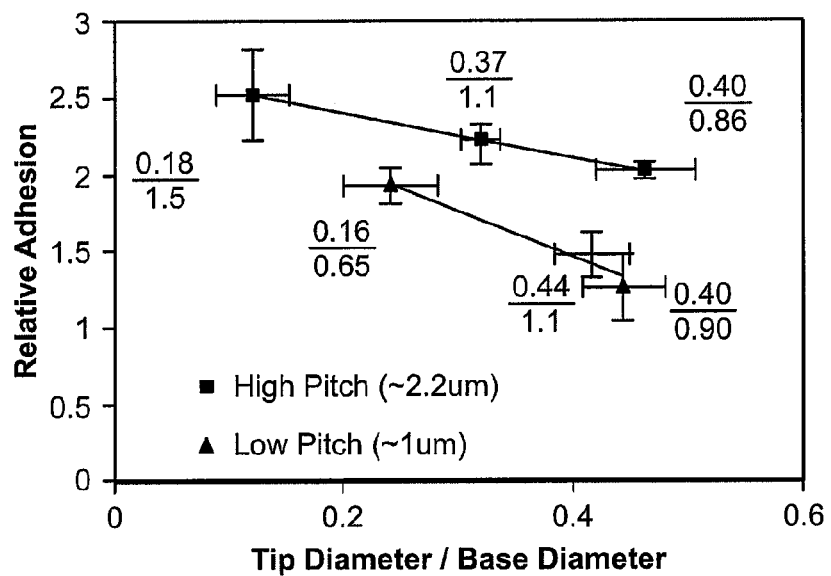
FIG. 7B depicts adhesion trends of 2.4-micrometers high protrusions as a function of tip width to base width ratio (T/B). Error bars in the y-direction indicate standard deviation of adhesion measurements; and error bars in the x-direction indicate standard deviation of measurements from optical profilometry measurements of protrusion size. $R^2$ values of linear fit for the low pitch and high pitch patterns are 0.96 and 0.99, respectively.
Figure 7C:
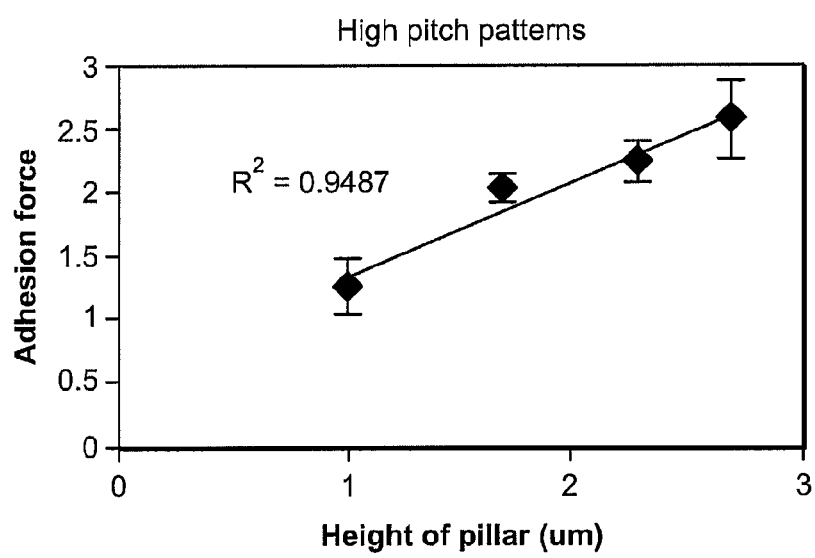
FIG. 7C depicts adhesion trends of protrusions having various configurations and dimensional parameters. The data in FIG. 6C are for the four highest pitch configurations of FIG. 7A. The $R^2$ value of linear fit is 0.95. Error bars in the y-direction indicate standard deviation of adhesion measurements; error bars in the x-direction indicate standard deviation of measurements from optical profilometry measurements of protrusion size.
Figure 7D:
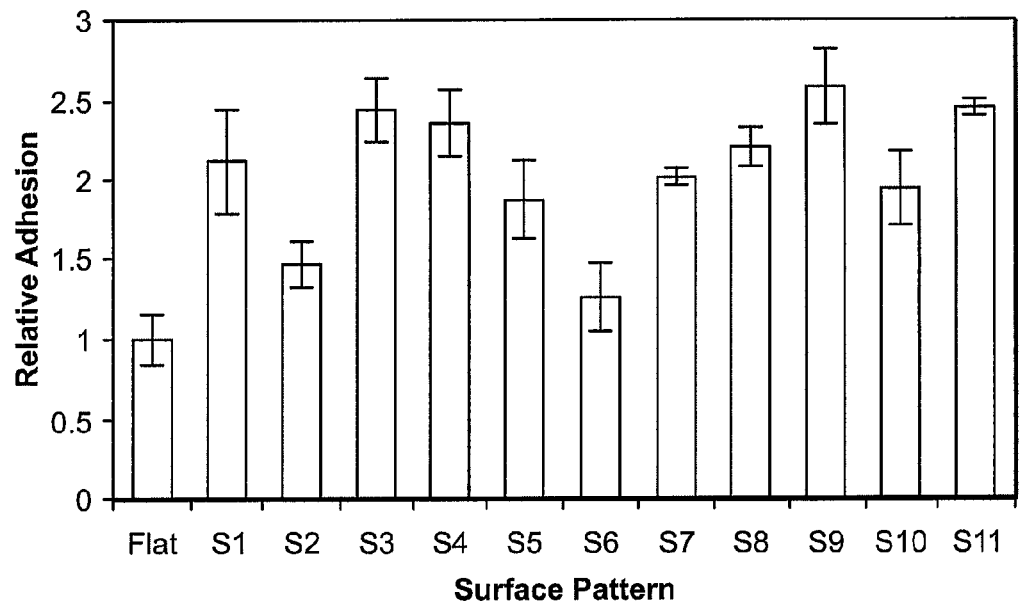

To provide Examples of tissue adhesion on area of contact, various of the Examples tested tissue adhesion strength as a function of tip diameter to pitch length for the patterns with the longest protrusions (2.4 µm). A decrease in the ratio of tip diameter to pitch leads was observed to lead to a decrease in tissue adhesion. Patterned adhesives may exhibit enhanced surface area of contact with tissue when the distance between pillars are sufficiently large and the tip diameter sufficiently low. The effect of protrusion geometry on adhesion independent of protrusion height, was measured by measuring adhesion as a function of ratio of tip diameter to base diameter. Referring to FIG. 7B, an increase in the tip diameter/base diameter ratio was observed to lead to a decrease in adhesion, and this trend was observed to hold at different pitch lengths. A decrease in pitch was observed to lead to a decrease in overall adhesion, as well as a sharper fall in adhesion strength with increasing tip diameter to base diameter ratios, as illustrated in FIG. 7B. Of the patterns tested, Pattern 9 from FIG. 7A provided the highest tissue adhesion and was subsequently used as the microstructured substrate in the Examples that follow (e.g., FIG. 7D).

Example 2

Surface Modification of Microstructured Substrate (Pattern 9)

Figure 8A:
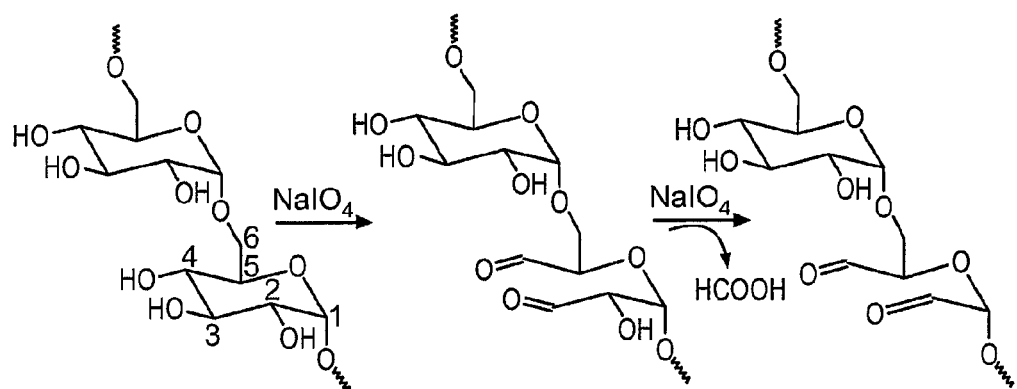
FIG. 8A schematically illustrates oxidation of dextran by sodium periodate, which attacks one of the hydroxyl groups of the vicinal triol in dextran residues, between $C_3$-$C_4$ or $C_2$-$C_3$, breaks the C—C bond, and yields two aldehyde groups. The product is dextran functionalized with aldehyde groups, referred to as DXTA.

In this Example, a microstructured substrate made of PGSA and of Pattern 9 (FIG. 7A) was coated with a thin layer of dextran oxidized (DXTA), which has aldehyde functionalities (FIG. 8A), to provide covalent bonding (e.g., crosslinking) with biological tissue. The terminal aldehyde groups in DXTA can react with resident amine groups in proteins to form imine bonds. Some of the aldehyde groups of DXTA can form a hemiacetal bond with free hydroxyl groups from the glycerol subunit on the PGSA polymer surface.

Figure 8B:
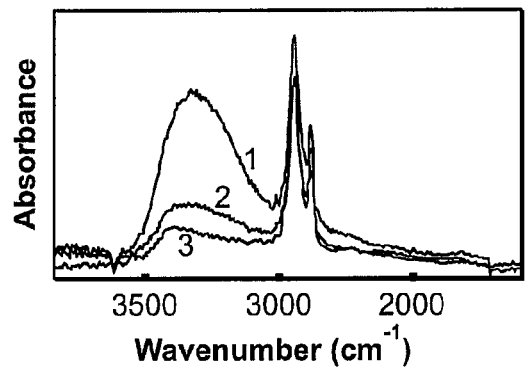
FIG. 8B presents Fourier transformed infrared (FTIR) spectroscopy spectra of a PGSA network coated with DXTA (1,2) or dextran (3), before (1) or after being washed with water (2,3). Higher absorbance at 3300 $cm^{-1}$ (normalized by the absorbance at 2930 $cm^{-1}$ corresponding to the stretching of C—H bonds) in PGSA patterns coated with DXTA than with dextran is indirect evidence that DXTA remained on the surface of the PGSA to a greater extent than dextran, after washing.

DXTA with a degree of oxidation of 14% (number of aldehyde groups per 100 glucose units in dextran), as confirmed by $^1$H-NMR and titration, was coated on the surface the microstructured substrate via spin coating. The DXTA-coated patterns were then rinsed extensively with deionized water and characterized by Fourier-Transform Infra-Red Spectroscopy (FTIR) (FIG. 8B). The peak at about 3300 cm$^{-1}$, corresponding to the stretching of O—H in the glucose units of dextran, was used to verify the immobilization of DXTA in the PGSA patterns. The higher absorbance at 3300 cm$^{-1}$ in PGSA nanopatterns coated with DXTA than those coated with non-oxidized dextran shows that DXTA remains on the surface of the PGSA pattern. A modified anthrone method of carbohydrate quantification (Somani et al. (1987) A modified anthrone-sulfuric acid method for the determination of fructose in the presence of certain proteins. *Anal Biochem* 167, 327-330) was used to determine that approximately 40 µg of DXTA was immobilized per cm$^2$ of projected area of the substrate (see FIG. 8C), after coating the substrates with a 55 (w/w) aqueous solution of DXTA and then rinsing with water.

Figure 8C:
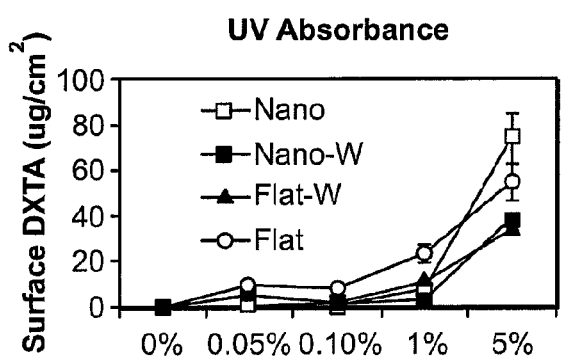
FIG. 8C presents data on quantification of the amount of DXTA on the surfaces of the washed patterned PGSA polymer. The data was determined using a modified anthrone technique for quantification of carbohydrates. Ultraviolet (UV) absorbance was measured for colorimetric quantification of DXTA concentration, and calibration curves at various time intervals wee obtained. A 19 minute time point was used for calibration. The DXTA amount can be estimated through a linear fit of UV absorbance observed after a reaction time of 19 minutes.
Figure 8D:
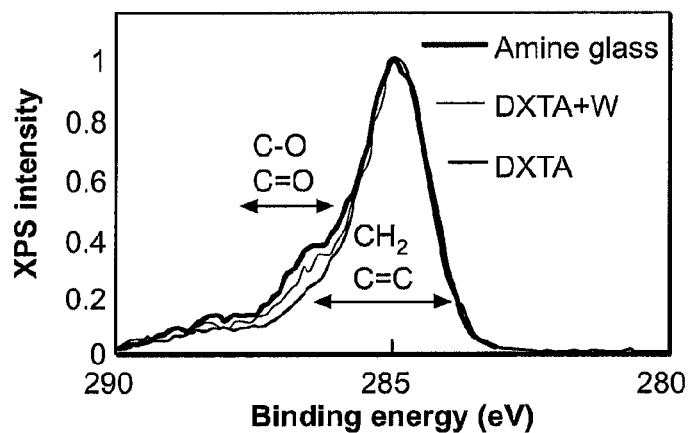
FIG. 8D presents C1s high resolution X-ray photoelectron spectroscopy (XPS) spectra of amine-functionalized glass and amine-functionalized glass coated with DXTA, before and after washing with water. The shift in spectra at positions 286 to 288 eV, corresponding to a carbon-oxygen bond, shows the presence of DXTA on the surface after washing with water (DXTA+W). Data was normalized to the C—C and $CH_2$ spectra peak at 285 eV.

Angle-resolved X-ray photoelectron spectroscopy (XPS) was used to verify the formation of imine bonds between surface bound amine groups and the aldehyde groups on the surface of DXTA-coated adhesive articles Amine-coated glass with a uniform surface density of at least 2×10$^{13}$ amine groups per mm$^2$ was used to represent the amine groups on a biological tissue surface. The presence of imine bond can be inferred from the DXTA that remains immobilized after rinsing the surface of DXTA-coated amine glass. The slight shift that occurs in the C(1s) peak at the C—O and C═O was used as an indication for presence of DXTA. Referring to FIG. 8D, a quantity of DXTA coated on the surface of the amine glass was observed to remain after rinsing the surface with water. In comparison, coating the glass surface with non-oxidized dextran polymer, which lacks the aldehyde functionality, does not result in immobilization of dextran on the surface of amine glass. Therefore, these results are indicative of effectiveness of introducing aldehyde functionalities/groups in the potential formation of bonds with a tissue surface.

Example 3

Adhesive Characterization of DXTA Modified Surfaces and Wet Adhesion

Figure 9B:
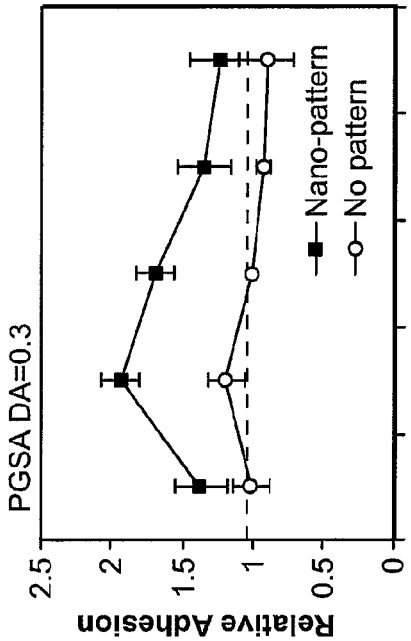
FIGS. 9A, 9B, and 9C present data on relative adhesion of patterned PGSA polymer vs. unpatterned PGSA polymer to porcine tissue slides as a function of DXTA surface coating concentration, where FIG. 9A provides data for a 0.8 degree of acrylation PGSA (PGSA DA=0.8)
Figure 9D:
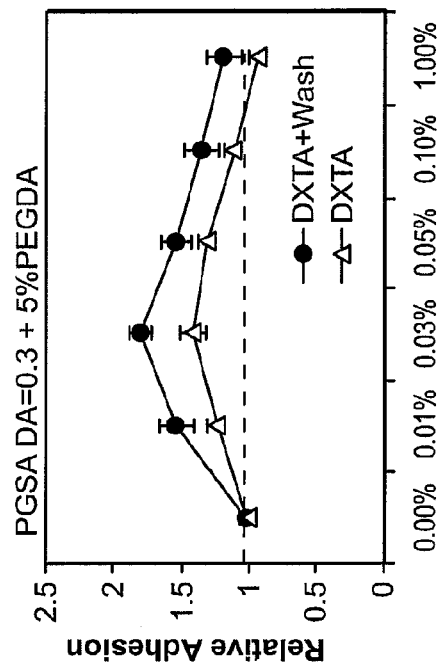
FIG. 9D presents normalized adhesion results of PGSA DA=0.3 with 5% PEGDA showing the effect of washing on improving adhesion at various DXTA surface coating concentrations. Data in FIGS. 9A-D are normalized to unpatterned 0.8 PGSA polymer without DXTA coating.
Figure 9A:
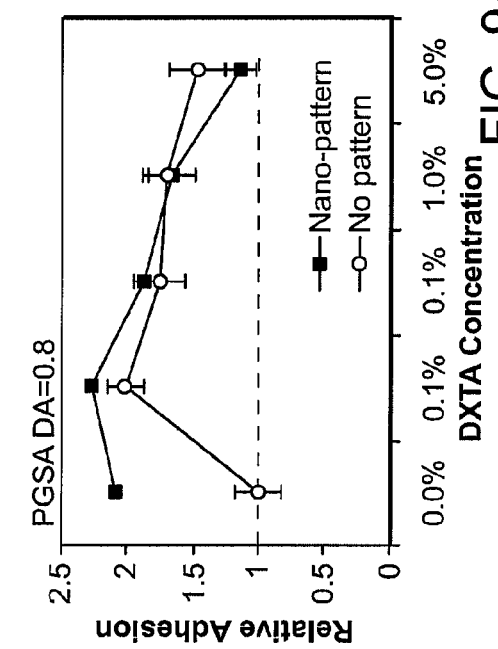

To determine the relative contribution of morphology and chemistry (e.g., modification with DXTA) to tissue adhesion, shear adhesion tests on porcine intestinal tissue were performed on different PGSA polymer compositions with various elastic properties. Three different compositions of PGSA were tested as defined by the prepolymer degree of acrylation (DA) including DA=0.3 and DA=0.8, which have low and high elastic moduli of 0.148 MPa and 1.375 MPa, respectively. Nijst C L, Bruggeman J P, Karp J M, Ferreira L, Zumbuehl A, Bettinger C J, Langer R. Synthesis and Characterization of Photocurable Elastomers from Poly(glycerol-co-sebacate), Biomacromolecules 2007; 8(10):3067-3073. The PGSA DA=0.8 is more hydrophobic and has slower degradation kinetics in vivo. Also tested was a PGSA DA=0.3 composition with 5% polyethylene glycol diacrylate (PEGDA), which has slower in vivo degradation kinetics and is more hydrophilic, with a higher elastic modulus. Referring to FIG. 9A, at DA=0.8, tissue adhesion tests demonstrated a modest increase in adhesion at various DXTA concentrations as compared to the non-patterned substrate (separation force=⅓×10$^4$N/m$^2$). The effect of patterning on increasing adhesion force can be observed at the 0% DXTA concentration values (maximum of ~two-fold). At the highest DXTA coating concentration of 5% (w/vol.), a decrease in adhesion was observed. PGSA DA=0.8 have less hydroxyl groups available (due to high incorporation of sebacic acid) and therefore less anchorage points for the immobilization of DXTA, which might explain the low effect of DXTA in PGSA DA=0.8. In contrast to the PGSA DA=0.8, a consistent increase in adhesion was observed for the microstructured PGSA DA=0.3 substrate in comparison to the non-patterned (non-microstructured) substrate as shown in FIG. 9B. The adhesion profile of the PGSA DA=0.3+PEG was similar to that of DA=0.8 polymer as shown in FIG. 8C. In all three examples, the highest adhesion force was observed using the 0.05% DXTA solution.

Figure 9C:
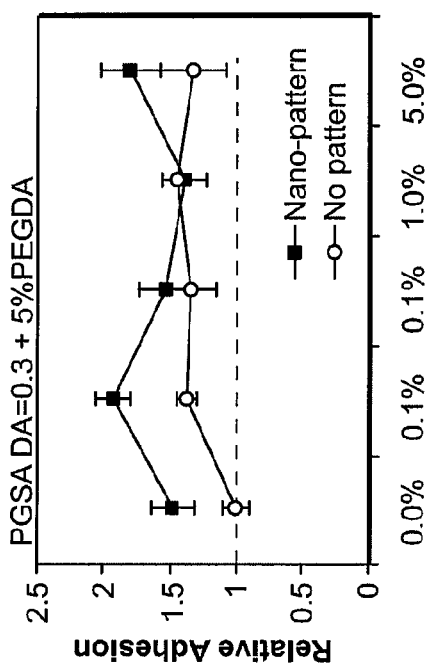
Figure 9E:
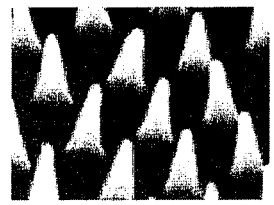
FIGS. 9E and 9F are SEM images, at different magnifications, of patterned PGSA polymer after surface spin coating with water as a control.
Figure 9F:
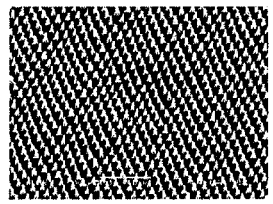
Figure 9G:
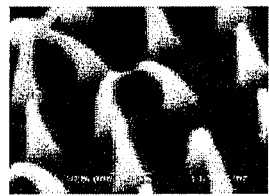
FIGS. 9G and 9H are SEM images, at different magnifications, of patterned PGSA after surface spin coating with 0.05% DXTA solution that show adhesion of neighboring protrusions.
Figure 9H:
Figure 9I:
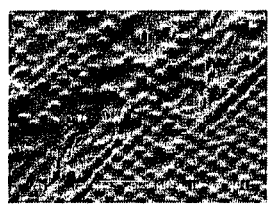
FIG. 9I is an SEM image that shows that, at a higher DXTA concentration of 5%, the patterned surface is obstructed by a thick DXTA coating.

As shown in FIG. 9C, a significant cumulative enhancement of morphology and chemistry was only observed at the 0.05% DXTA concentration for PGSA DA=0.3 with 5% PEGDA. The increased adhesion may also have resulted from mechanical interlocking due to polymer swelling from the PEG component. It has been shown that a 50% increase in swelling ratio with the addition of 5% PEG to PGSA DA=0.3 (i.e., from 10% to 15%). Autumn K, Liang Y A, Hsieh S T, Zesch W, Chan W P, Kenny T W, Fearing R, Full R J. Adhesive force of a single gecko foot-hair Nature 2000; 405(6787): 681-5. In the compositions of PGSA DA=0.3 (FIG. 8B) and PGSA DA=0.3 with 5% PEGDA, the highest adhesion force was observed using the 0.05% DXTA solution. Quantitatively, a maximum enhancement of ~2 relative to non-patterned surfaces without the DXTA coating was observed for the both PGSA DA=0.3 ($4.8 \times 10^4$ N/m$^2$ for the patterned vs. $2.5 \times 10^4$ N/m$^2$ for non-patterned non-DXTA coated) and PGSA DA=0.3+5% PEG ($3.5 \times 10^4$ N/m$^2$ for the patterned vs. $1.8 \times 10^4$ N/m$^2$ for non-patterned non-DXTA coated).

To determine if washing affects (e.g., improves) adhesion through removal of excess DXTA, the coated surface of a PGSA DA=0.3+PEG microstructured substrate was rinsed with deionized water and tissue adhesion tests were performed. Based on FIG. 9D, rinsing consistently improved adhesion, and the best coating observed was determined to be 0.025% solution of DXTA followed by removal of excess DXTA through rinsing with deionized water, which led to a four-fold enhancement in adhesion over native DA=0.8 surfaces. SEM images of DXTA-coated PGSA nano-patterns revealed that at low DXTA concentrations of 0.05%, protrusion tip interactions occur in about 50% of the protrusions. However, at a high DXTA concentration of 5%, the protrusions are covered by a thick layer of DXTA coating, which prevented the underlying patterns from contacting the tissue. This observation is a possible explanation for the decrease in adhesion observed for the 5% DXTA coated patterns. Table 1 shows the baseline and maximum adhesion strength values achieved for each material tested.

TABLE 1

| Polymer | Native Separation Force Without Pattern or DXTA | Maximum Separation Force With Pattern and DXTA |
| --- | --- | --- |
| PGSA DA = 0.8 | $1.3 \times 10^4$ N/m$^2$ | $2.9 \times 10^4$ N/m$^2$ |
| PGSA DA = 0.3 | $2.5 \times 10^4$ N/m$^2$ | $4.8 \times 10^4$ N/m$^2$ |
| PGSA DA = 0.3 + 5% PEGDA | $1.8 \times 10^4$ N/m$^2$ | $3.5 \times 10^4$ N/m$^2$ |

Example 4

Protrusion Collapse Effects in Wet Adhesion

To investigate collapse of wet protrusions, optical profilometry images of patterns were obtained during the drying process. Protrusion collapse occurs on the surface of the pattern after drying. Whereas in DXTA-mediated protrusion contact between neighboring protrusions (through adjoining tips), water evaporation results in complete protrusion collapse onto the surface of the PGSA polymer such that the protrusions can be bent to contact article 20 along its length. Surface evaporation of liquids can provide a method to achieve such geometries. Time-lapsed optical profilometry imaging showed that surface water on the pattern is segregated into small droplets (which are formed between several neighboring protrusions). Further drying of these small droplets resulted in collapse of the protrusions into small clusters that were evenly distributed on the surface. This process was observed to be reversible as reintroduction of water to the surface resulted in separation of collapsed protrusions and restoration of the original pattern. However it is possible to use this effect to achieve certain desired geometries. Hence, this reversibility obviated the need to further modify the PGSA microstructured substrate to reduce protrusion collapse for wet adhesion.

In various embodiments, the adhesive articles take advantage of this behavior to provide an adhesive article with an adhesive strength in water that is greater than the adhesive strength in air. Uses of such an article include, e.g., an adhesive article that is substantially non-adhesive in a dry state (for example, in a package) that can be readily handle by a user, but when the article is placed in contact with a biological tissue (an in vivo tissue that, as used herein, is considered to be "in water"), the adhesive article becomes adhesive.

Example 5

Degradation Characteristics of Adhesive Articles

Figure 10A:
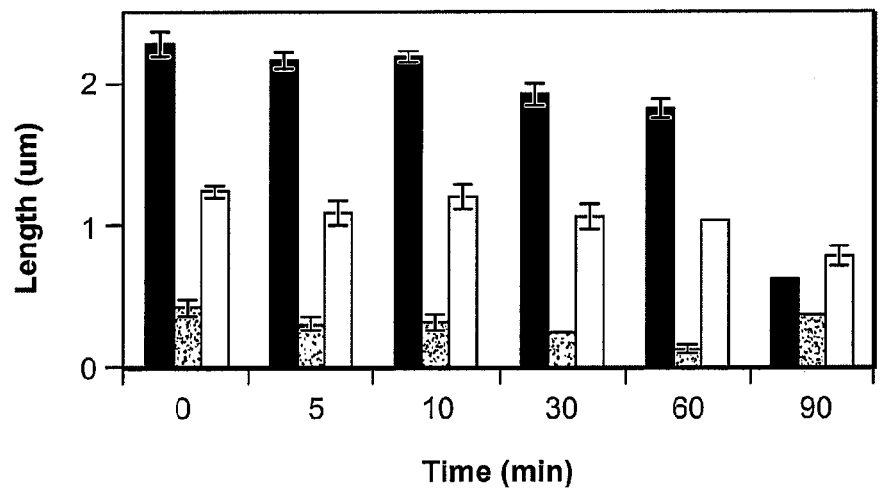
FIG. 10A presents data from time-lapsed optical profilometry measurements of protrusion dimensions during in vitro degradation in a 1N solution of sodium hydroxide showing protrusion height (leftmost bar), protrusion base width (middle bar), and protrusion tip width (rightmost bar). Error bars represent one standard deviation from at least ten different protrusions measurements.
Figure 10B:
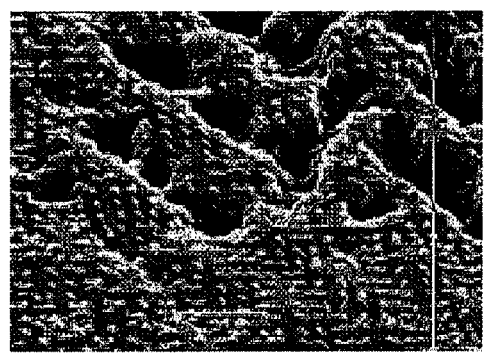
FIG. 10B presents an SEM image of a PGSA DA=0.3 patterned surface after eight days of in vitro degradation under physiological conditions in 25 U/ml of cholesterol esterase enzyme. The scale bar represents 10 micrometers.

To understand how the adhesive articles change as a function of biodegradation, changes in protrusion geometry were investigated. Microstructured PGSA substrates were degraded in 1N solution of sodium hydroxide, and time-lapsed optical profilometry was used to measure protrusion dimensions concurrently. Referring to FIG. 10A, protrusion height decreased during degradation while there was only a slight decrease in the base diameter. A decrease in protrusion height resulted in an increase in protrusion tip diameter since these protrusions were cone shaped. To investigate pattern degradation in more physiologically relevant conditions, we subjected the PGSA DA=0.3 microstructured substrates to degradation in 1 U/ml of cholesterol esterase enzyme. Cholesterol esterase enzyme has been shown to be identical to the esterases associated with macrophages that are known to degrade polyesters. After eight days of degradation, SEM images of the patterns, as shown in FIG. 10B, revealed that protrusions are present after the bulk underlying PGSA material has started to degrade. In PGSA DA=0.8 and PGSA DA=0.3 with 5% PGDA formulations (data not shown), no observable degradation of protrusions was observed to occur in eight days.

Example 6

Biocompatibility of Adhesive Articles

Biocompatibility of various embodiments of the adhesive articles, referred to in this Example as tissue tape, were assessed through implantation of 1 cm$^2$ patches of tissue tape in the subfascial environment overlying the rectus muscle of rats, selected for its clinical relevance. The tissue tapes were cut into square patches and inserted into fascial flaps on the underlying rectus muscle with the microstructured substrates oriented outward toward the fascia.

The aim was to determine the effect of the microstructured substrate surfaces and the DXTA coating on tissue biocompatibility and adhesiveness. Adhesive strength was determined as described above, where explanted tissue containing the adherent patch was fixed on a glass slide and a defined mechanical force applied. Weight loss measurements of the tissue tapes after one week implantation showed negligible difference between the PGSA DA=0.3 and PGSA DA=0.3+ PEG microstructured substrates. The PGSA with the higher degree of acrylation (0.8) had a smaller weight loss which is indicative of slower degradation (FIG. 11A). To determine if the improved adhesion from the DXTA coating was maintained over time, adhesion tests were performed on the tissue tape after 48 hours of implantation. Referring to FIG. 11B, the adhesive strength of DXTA coated microstructured substrates were more than two fold higher than samples without the DXTA coating.

As the results in FIG. 7B suggest, a decrease in the tip diameter to pitch ratio (T/P) leads to an enhancement in adhesion. In other words, maximum enhancement occurs for the pattern with the lowest density of pillars. This observation is counterintuitive since previous work on patterned adhesion demonstrated that enhancement is based on the mechanism of contact line splitting that favors maximizing the pillar density. However, for these materials, the pillars are interfacing with another soft, compliant surface, namely, the deformable tissue, so one possible means of enhancement is associated with the enhanced conformal contact between the tissue and PGSA patterned adhesive. The tissue can better conform to the patterned adhesive surface when the distance between pillars are sufficiently large and the tip diameter sufficiently low. Otherwise, the tissue may not conform to the area between the pillars, and the interfacial contact area is reduced. Hence, for a constant pillar height, the T/P ratio is an empirical descriptor that describes the ability of the tissue interface to conform to the patterned surface and the increased interfacial contact area. Although this mechanism differs from the adhesion mechanism observed in contact line splitting (as with a gecko, for example), their principles of adhesion enhancement are similar: design of a patterned interface to enhance interfacial contact.

To determine if the improved adhesion from DXTA coating was maintained over time, adhesion of the patterns was measured after 48 hr of implantation. As shown in FIG. 11B, the adhesive strength of DXTA-coated patterns was more than two-fold higher than samples without the DXTA coating.

To assess the effect of polymer composition and nanotopography on tissue response, disks of patterned PGSA polymer were implanted subcutaneously in the backs of rats for 7 days. The tissue response was mild (FIGS. 11C and 11D) and was not dependent on PGS nanotopography or formulation (FIGS. 11E-11H). A thin inflammatory infiltrate layer with little vascularization encircled the implant cavity. No giant cell reaction was observed. The chronic inflammation to non-resorbable polyurethane (FIG. 11H), which was used as a control, was more pronounced, as the cellular infiltrate surrounding the implant had a distinctive papillary architecture with increased vascularity and edema. The tissue response was not assessed in the functional tests for the materials that were implanted in the preperitoneal space. This functional model provided the benefit of evaluating the adhesiveness of the material in contact with two different tissue surfaces. Extensive surgical manipulation of the tissue was used, which induced some expected muscle degradation with marked fibroblastic proliferation that masked any inflammatory response to the implanted materials. Taken together, these results suggest that introduction of patterned substrates or the DXTA coating on the surface of the PGSA polymer did not result in an increased tissue response to the implant. Therefore, a general strategy of using a judicious choice of surface patterning with tissue compatible surface chemistry can provide an effective means to achieve tissue adhesion.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

Other embodiments are within the scope of the following claims.

What is claimed is:

1. An adhesive article comprising:
   a biocompatible and at least partially biodegradable substrate having a surface and protrusions extending from the surface;
   wherein the protrusions comprise a biocompatible and at least partially biodegradable material,
   wherein the protrusions have an average height of less than approximately 1,000 μm, and
   wherein the protrusions have a tip width to pitch ratio (T/P) ranging from about 0.8 to about 0.1.

2. The adhesive article of claim 1, wherein the tip width to pitch ratio (T/P) is from about 0.6 to about 0.2.

3. The adhesive article of claim 1, wherein the protrusions have an average tip width of from approximately 0.05 μm to approximately 10 μm.

4. The adhesive article of claim 1, wherein the protrusions have an average base width of from approximately 0.05 μm to approximately 10 μm.

5. The adhesive article of claim 1, wherein the protrusions have a base width to tip width ratio (B/T) in the range of from about 2:1 to about 20:1.

6. The adhesive article of claim 1, wherein the protrusions have an average height of from approximately 0.25 μm to approximately 10 μm.

7. The adhesive article of claim 1, wherein the protrusions have an average center-to-center pitch from approximately 0.2 μm to approximately 100 μm.

8. The biocompatible adhesive article of claim 1, wherein the substrate comprises poly(glycerol sebacate) (PGS), poly (glycerol sebacate acrylate) (PGSA), poly(lactic-co-glycolic acid) (PLGA), polycaprolactone (PCL), polyglycolide (PGA), polylactic acid (PLA), poly-3-hydroxybutyrate (PHB), star-poly-caprolactone-co-D,L-lactide, poly(tri-methyl carbonate-co-caprolactone), poly(ethylene glycol) (PEG), polyurethane, parylene-C, poly(citric-diol), hyaluronic acid, dextran, chitosan, alginate, keratin, carbon nanotubes, or agrose.

9. The adhesive article of claim 1, wherein the biocompatible adhesive article further comprises a biomolecule or a pharmaceutical compound.

10. The adhesive article of claim 9, wherein the biomolecule or pharmaceutical compound is selected from the group consisting of anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or antiprotozoal compounds, modulators of cell-extracellular matrix interactions including cell growth inhibitors and pro- or anti-adhesion molecules, vasodilating agents, inhibitors of DNA, RNA or protein synthesis, anti-hypertensives, analgesics, anti-pyretics, steroidal and non-steroidal anti-inflammatory agents, pro- or anti-angiogenic factors, pro- or anti-secretory factors, anticoagulants and/or anti-thrombotic agents, local anesthetics, ophthalmics, prostaglandins, antidepressants, anti-psychotic substances, anti-emetics, growth factors, proton pump inhibitors, hormones, vitamins, gene delivery systems, and imaging agents.

11. The adhesive article of claim 1, further comprising a plurality of cells.

12. The adhesive article of claim 11, wherein the plurality of cells comprises one or more kerotinocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, stem cells, neurobalstoma, chondrocytes, skin cells and bone-forming cells.

13. The adhesive article of claim 1, further comprising an adherent layer having a moiety capable of bonding to the biological tissue.

14. The adhesive article of claim 13, wherein the moiety capable of bonding to the biological tissue comprises aldehydes.

* * * * *